(12) United States Patent
Sato

(10) Patent No.: US 6,878,822 B2
(45) Date of Patent: Apr. 12, 2005

(54) ETHYLENE DERIVATIVE HAVING A NITROGEN-CONTAINING 7-MEMBERED RING

(75) Inventor: Tadahisa Sato, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 390 days.

(21) Appl. No.: 10/141,001

(22) Filed: May 9, 2002

(65) Prior Publication Data

US 2003/0065171 A1 Apr. 3, 2003

Related U.S. Application Data

(62) Division of application No. 09/413,848, filed on Oct. 7, 1999, now Pat. No. 6,413,657.

(30) Foreign Application Priority Data

Oct. 7, 1998 (JP) ........................... P. 10-285508
Mar. 29, 1999 (JP) ........................... P. 11-86607

(51) Int. Cl.$^7$ ........................................... C07D 223/18
(52) U.S. Cl. ................................. 540/576; 540/587
(58) Field of Search ........................... 540/484, 576, 540/586, 587

(56) References Cited

U.S. PATENT DOCUMENTS 5,929,235 A  7/1999  Sato ..................... 540/576

FOREIGN PATENT DOCUMENTS

| JP | 3-196047 A | * | 8/1991 |
| JP | 5-181292 A |   | 7/1993 |
| JP | 9-295969 A |   | 11/1997 |
| JP | 10-59943 A |   | 3/1998 |
| JP | 10-59952 A |   | 3/1998 |
| JP | 11-3049 A  |   | 1/1999 |
| JP | 11-26163 A |   | 1/1999 |

* cited by examiner

Primary Examiner—Marie Yamnitzky
(74) Attorney, Agent, or Firm—Sughrue Mion, PLLC

(57) ABSTRACT

A compound represented by formula (IA):

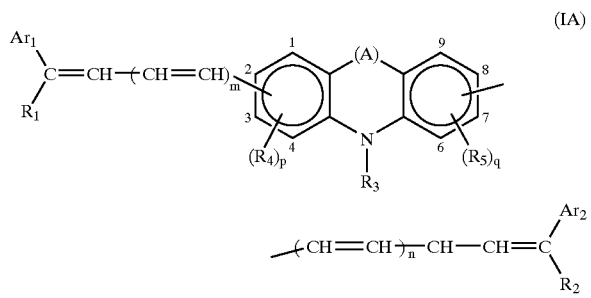

in which (A) represents an ethylene group, a vinylene group or an o-arylene group; $Ar_1$ and $Ar_2$ each represent an aryl group; $R_1$ and $R_2$ each represent an alkyl group or an aryl group; $R_3$ represents an alkyl group or an aryl group; $R_4$ and $R_5$ each represent a halogen atom, an alkyl group, an aryl group, an alkoxy group, an aryloxy group, a dialkylamino group, an N-alkyl-N-arylamino group or a diarylamino group; or $Ar_1$ and $R_1$, or $Ar_2$ and $R_2$ are taken together either directly or indirectly to form a ring; $Ar_1(R_1)C=CH-(CH=CH)_m-$ and $Ar_2(R_2)C=CH-(CH=CH)_n-$ are on the 2- or 3-position and the 7- or 8-position of the respective benzene rings; m and n each represent an integer of from 0 to 2; and p and q each represent an integer of from 0 to 3.

22 Claims, No Drawings

ETHYLENE DERIVATIVE HAVING A NITROGEN-CONTAINING 7-MEMBERED RING

This is a divisional of application Ser. No. 09/413,848 filed Oct. 7, 1999, now U.S. Pat. No. 6,413,657; the disclosure of which is incorporated herein by reference.

BACKGROUND OF THE INVENTION

1. Field of the Invention

This invention relates to a light-emitting material capable of converting electric energy to light (luminescent element material) and a luminescent element comprising the same. More particularly, this invention relates to a luminescent element (device) suited for use in the fields of display elements, displays, back lights, electrophotography, lighting sources, recording light sources, reading light sources, labels, signboards, interior decorations, and the like.

This invention also relates to an ethylene derivative having a nitrogen-containing 7-membered ring which is useful as a charge transporting compound in an electrophotographic photoreceptor, an organic electroluminescent element, etc.

This invention also relates to a benzoazepine derivative having a vinyl group, which can be a raw material of polymer useful as an electrophotographic photoreceptor, an organic electroluminescent element, etc.

2. Description of the Related Art

Today various display devices have been researched and developed. Inter alia an organic luminescent element has been attracting attention as a promising means for obtaining electroluminescence of high brightness at a low driving voltage. For example, a luminescent element comprising an organic compound in a thin film formed by vacuum evaporation (see *Appl. Phys. Lett.*, vol. 51, p. 913 (1987)). However, production of an organic luminescent element involving vacuum evaporation of an organic compound has a problem of productivity. From the standpoint of simplification of production process, processability, and increase of a display area, production of an organic luminescent element by a coating system is desirable.

Known luminescent element materials useful in the production of luminescent elements by a coating system, which is advantageous for productivity, include π-conjugated polymers typically exemplified by p-phenylenevinylene. However, having a light-generating part in the polymer main chain, the π-conjugated polymers have difficulty in controlling concentration so that it is difficult to delicately control the color tone and luminescent intensity.

Luminescent elements prepared by the coating system also include those comprising a low-molecular fluorescent compound dispersed in poly(N-vinylcarbazole) (JP-A-4-212286). Because this mode permits free alteration of the fluorescent compound species, it is relatively easy to control the color tone and luminescent intensity. However, the luminescent elements of this mode require a high driving voltage and involves a problem of durability such that the brightness tends to decrease when the element resumes operation after long suspension or when the element is operated continuously.

Photoconductors that have been used in electrophotographic photoreceptors chiefly include inorganic substances such as selenium, cadmium sulfide, and zinc oxide. Electrophotographic photoreceptors are essentially required (i) to be charged in appropriate positions thereof in the dark, (ii) to hardly dissipate the charges in the dark, and (iii) to be able to dissipate the charges quickly upon being irradiated. Photoreceptors comprising the inorganic photoconductors possess many merits and demerits. For example, the demerits of widely used selenium photoreceptors, while well satisfying the requirements (i) to (iii), lie in (1) strict conditions of production, which leads to a high cost of production, (ii) lack of flexibility, which makes it difficult to obtain a belt photoreceptor, and (iii) sensitiveness to a thermal or mechanical shock, which necessitates careful handling. While cadmium sulfide and zinc oxide have been used as dispersed in a binder resin, they cannot withstand alone repeated use due to their mechanical drawbacks in terms of smoothness, hardness, tensile strength, and abrasion resistance.

To solve these problems, electrophotographic photoreceptors comprising various organic photoconductors have recently been proposed, and some of them have been put to practical use. Organic photoreceptors so far developed include one comprising poly-N-vinylcarbazole and 2,4,7-trinitrofluoren-9-one (U.S. Pat. No. 3,484,237), one comprising poly-vinylcarbazole sensitized with a pyrylium salt dye (JP-B-48-25658), one mainly comprising an organic pigment (JP-A-47-37543), one mainly comprising an eutectic complex of a dye and a resin (JP-A-47-10735), one mainly comprising a hydrazone compound (JP-A-57-101844 and JP-A-54-150128), one mainly comprising an aromatic tertiary amine compound (JP-B-58-32372), and one mainly comprising a stilbene compound (JP-A-58-198043). Although these photoreceptors exhibit excellent characteristics and appear to have high practical values, they are not fully satisfactory taking the latest various requirements for photoreceptors into consideration. Hence the studies on electrophotographic organic photoreceptors are still being continued. For example, one can find from the recent literature novel hydrazone compounds (JP-A-8-143550), carbazole type stilbene compounds (JP-A-8-59615 and JP-A-9-295969), and tri-substituted ethylene compounds (JP-A-63-225660, JP-A-5-181292, JP-A-9-59256, and JP-A-10-59952).

U.S. Pat. No. 4,539,507 to VanSlyke et al. discloses that a multi-layer type organic luminescent element having a hole-injecting and transporting zone comprising an aromatic tertiary amine containing a phenyl group, a phenylene group or a biphenylene group exhibits stabilized light output and thereby a prolonged service life. To further improve the light output stability, efforts have been made by many researchers to add improvements to the aromatic tertiary amines to be used in the hole-injecting and transporting zone, resulting in a large number of patent applications and reports in the professional literature. For example, improvements on biphenyl type tertiary amines are found in *Japanese Journal of Applied Physics*, vol. 27, L269 (1988), JP-A-59-194393, *Appl. Phys. Lett.*, vol. 66, p. 2679 (1995), JP-A-5-234681, JP-A-7-331238, JP-A-8-48656, and WO95/09147; and improvements on star burst type tertiary amines are disclosed in *Appl. Phys. Lett.*, vol. 65, p. 807 (1994), and JP-B-7-110940. However, the compounds known from the literature cannot be said to have sufficient performance, still leaving room for further improvement.

An object of the invention is to provide a luminescent element material and a luminescent element that emit light of high brightness at a low driving voltage and exhibit excellent durability when used repeatedly.

Another object of the invention is to provide a novel ethylene derivative useful in an electrophotographic photoreceptor, an organic luminescent element, and the like.

A further object of the invention is to provide a novel ethylene derivative useful in an electrophotographic photoreceptor or an organic luminescent element and excellent in charge transporting ability and storage stability.

A still further object of the invention is to provide a benzoazepine derivative having a vinyl group which can be a raw material of polymer useful as an electrophotographic photoreceptor or an organic luminescent element.

The above objects of the invention is accomplished by the following means.

(1) A luminescent element material comprising a polymer having a partial structure represented by formula (I):

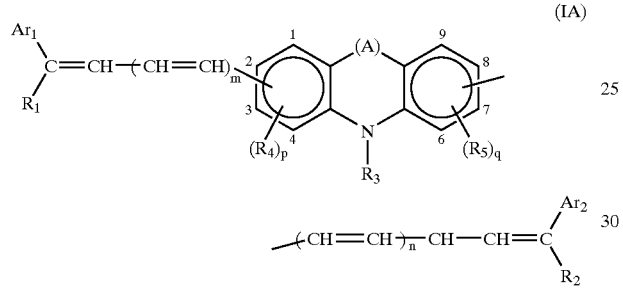

(2) A luminescent element material comprising a polymer having at least one repeating unit represented by formula (II):

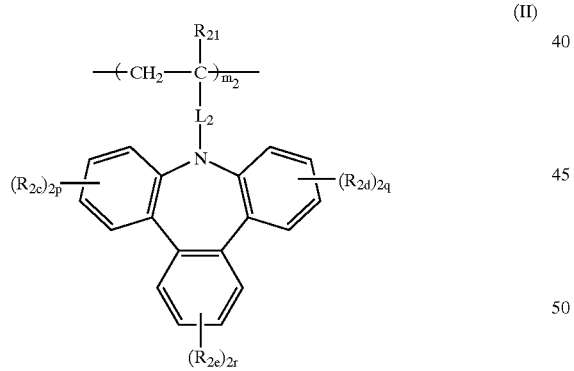

wherein $R_{2c}$, $R_{2d}$, and $R_{2e}$ each represent a substituent; 2p, 2q, and 2r each represent an integer of from 0 to 4; where 2p, 2q or 2r is 2 or greater, two or more $R_{2c}$'s, $R_{2d}$'s or $R_{2e}$'s may be the same or different; $L_2$ represents a single bond or a divalent linking group; $R_{21}$ represents a hydrogen atom, an alkyl group or an aryl group; and $m_2$ represents an integer of 1 or greater.

(3) A luminescent element material comprising a polymer containing at least one repeating unit represented by formula (III):

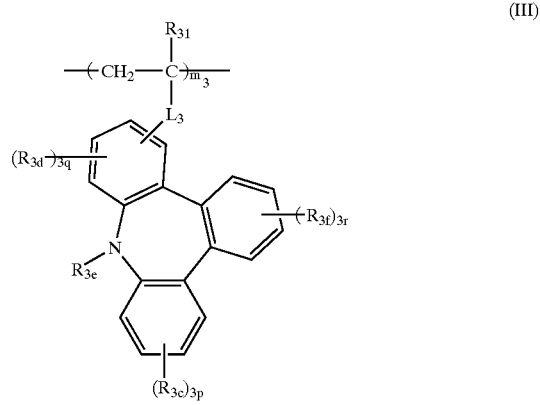

wherein $R_{3e}$ represents a hydrogen atom or a substituent; $R_{3c}$, $R_{3d}$, and $R_{3f}$ each represent a substituent; 3p and 3r each represent an integer of from 0 to 4; 3q represents an integer of from 0 to 3; where 3p, 3q or 3r is 2 or greater, two or more $R_{3c}$'s, $R_{3d}$'s or $R_{3f}$'s may be the same or different; $L_3$ represents a single bond or a divalent linking group; $R_{31}$ represents a hydrogen atom, an alkyl group or an aryl group; and $m_3$ represents an integer of 1 or greater.

(4) A luminescent element material comprising a polymer having at least one repeating unit represented by formula (IV):

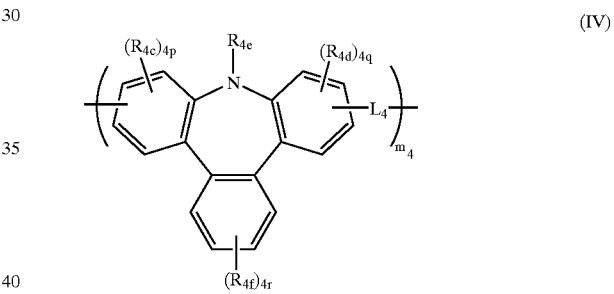

wherein $R_{4e}$ represents a hydrogen atom or a substituent; $R_{4c}$, $R_{4d}$, and $R_{4f}$ each represent a substituent; 4p and 4q each represent an integer of from 0 to 3; 4r represents an integer of from 0 to 4; where 4p, 4q or 4r is 2 or greater, two or more $R_{4c}$'s, $R_{4d}$'s or $R_{4f}$'s may be the same or different; $L_4$ represents a single bond or a divalent linking group; and $m_4$ represents an integer of 1 or greater.

(5) The luminescent element material according to (2) above, wherein $m_2$ in formula (II) is 6 to 100,000.

(6) The luminescent element material according to (3) above, wherein $m_3$ in formula (III) is 6 to 100,000.

(7) The luminescent element material according to (4) above, wherein $m_4$ in formula (IV) is 6 to 100,000.

(8) An luminescent element comprising a pair of electrodes having therebetween a luminescent layer or a plurality of organic compound thin layers containing a luminescent layer, wherein the luminescent layer or at least one of the plurality of thin layers contains the luminescent element material set forth in any one of (1) to (7) described above.

(9) A luminescent element comprising a pair of electrodes having therebetween a luminescent layer or a plurality of organic compound thin layers containing a luminescent layer, wherein the luminescent layer or at least one of the plurality of thin layers is a layer formed by coating with the luminescent element material set forth in any one of (1) to (7).

(10) An ethylene derivative having a nitrogen-containing 7-membered ring as represented by formula (IA):

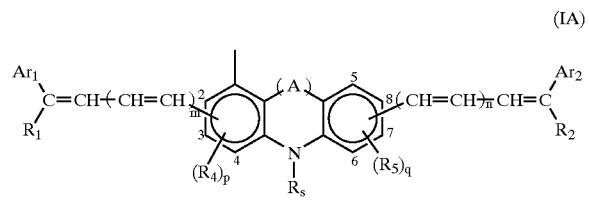

(IA)

wherein (A) represents an ethylene group, a vinylene group or an o-arylene group; $Ar_1$ and $Ar_2$ each represent an aryl group; $R_1$ and $R_2$ each represent an alkyl group or an aryl group; $R_3$ represents an alkyl group or an aryl group; $R_4$ and $R_5$ each represent a halogen atom, an alkyl group, an aryl group, an alkoxy group, an aryloxy group, a dialkylamino group, an N-alkyl-N-arylamino group or a diarylamino group; $Ar_1$ and $R_1$, or $Ar_2$ and $R_2$ may be taken together either directly or indirectly to form a ring; $Ar_1(R_1)C=CH-(CH=CH)_m-$ and $Ar_2(R_2)C=CH-(CH=CH)_n-$ are on the 2- and 3-positions and the 7- and 8-positions of the respective benzene rings; m and n each represent an integer of from 0 to 2; and p and q each represent an integer of from 0 to 3.

(11) A benzoazepine derivative represented by formula (IB):

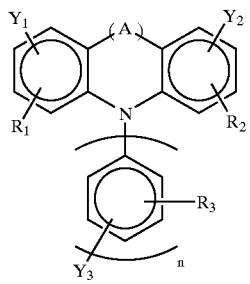

(IB)

wherein (A) represents a vinylene group or an o-arylene group; $R_1$, $R_2$, $R_3$, $Y_1$, $Y_2$, and $Y_3$ each represent a hydrogen atom or a substituent, provided that at least one of $Y_1$, $Y_2$, and $Y_3$ represents an ethenyl group; n represents an integer of from 1 to 4; when n=0, $Y_3$ represents an alkyl group, an aryl group or an ethenyl group.

DETAILED DESCRIPTION OF THE INVENTION

The luminescent element material according to the invention comprises a polymer having a partial structure represented by formula (I), hereinafter referred to as polymer A. The polymer A serves for light emission.

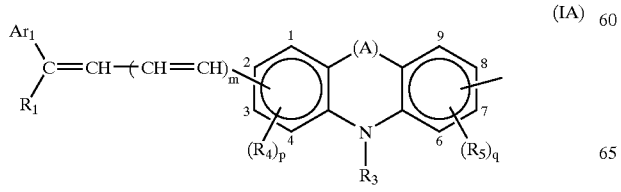

(IA)

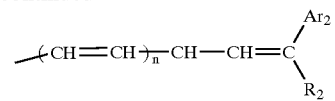

Polymer A has the partial structure represented by formula (I) in its main chain and/or side chain. Polymer A preferably contains at least one repeating unit represented by formula (II), (III) or (IV):

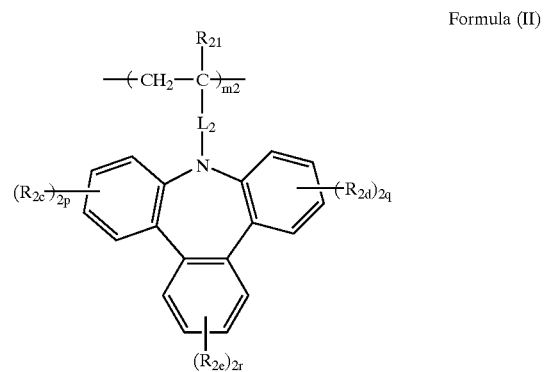

Formula (II)

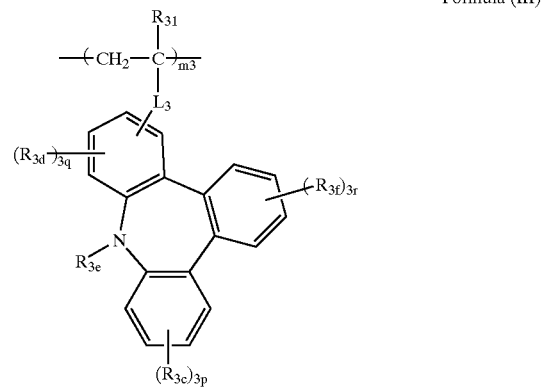

Formula (III)

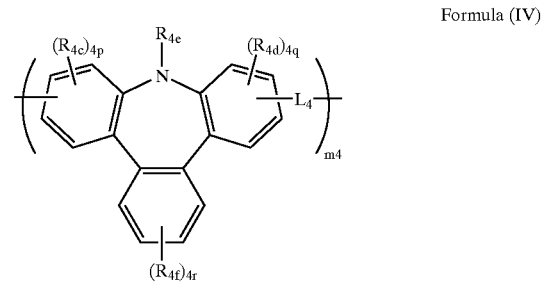

Formula (IV)

In formulae (II) to (IV), $R_{2c}$, $R_{2d}$, $R_{2e}$, $R_{3c}$, $R_{3d}$, $R_{3f}$, $R_{4c}$, $R_{4d}$, and $R_{4f}$ are individually a substituent. The substituent includes an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a sulfinyl group, a ureido group, a phosphoric acid amido group, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group, and a silyl group.

More specifically, the alkyl group preferably has 1 to 30, particularly 1 to 20, especially 1 to 10, carbon atoms, including methyl, ethyl, isopropyl, t-butyl, n-octyl, n-decyl, n-hexadecyl, cyclopropyl, cyclopentyl and cyclohexyl groups. The alkenyl group preferably contains 2 to 30, particularly 2 to 20, especially 2 to 10, carbon atoms, including vinyl, allyl, 2-butenyl, and 3-pentenyl groups. The alkynyl group preferably has 2 to 30, particularly 2 to 20, especially 2 to 10, carbon atoms, including propargyl and 3-pentynyl groups.

The aryl group preferably contains 6 to 30 carbon atoms, particularly 6 to 20 carbon atoms, especially 6 to 12 carbon atoms and includes phenyl, p-methylphenyl, and naphthyl groups. The amino group preferably has up to 30 carbon atoms, particularly up to 20 carbon atoms, especially up to 10 carbon atoms. Examples of the amino group are amino, methylamino, dimethylamino, diethylamino, dibenzylamino, diphenylamino, ditolylamino, di(4-methoxyphenyl)amino, N-phenyl-N-(1-naphthyl)amino, and N-phenyl-N-(1-thienyl)amino groups.

The alkoxy group preferably has 1 to 30, particularly 1 to 20, especially 1 to 10, carbon atoms, including methoxy, ethoxy, butoxy, 2-ethylhexyloxy groups. The aryloxy group preferably has 6 to 30, particularly 6 to 20, especially 6 to 12 carbon atoms, including phenyloxy, 1-naphthyloxy, and 2-naphthyloxy groups.

The acyl group preferably contains 1 to 30, particularly 1 to 20, especially 2 to 12, carbon atoms, including acetyl, benzoyl, formyl, and pivaloyl groups. The alkoxycarbonyl group preferably has 2 to 30, particularly 2 to 20, especially 2 to 12, carbon atoms, including methoxycarbonyl and ethoxycarbonyl groups. The aryloxycarbonyl group preferably has 7 to 30, particularly 7 to 20, especially 7 to 12, carbon atoms, including a phenyloxycarbonyl group. The acyloxy group preferably has 2 to 30, particularly 2 to 20, especially 2 to 10, carbon atoms, including acetoxy and benzoyloxy groups.

The acylamino group preferably has 2 to 30, particularly 2 to 20, especially 2 to 10, carbon atoms, including acetylamino and benzoylamino groups. The alkoxycarbonylamino group preferably has 2 to 30, particularly 2 to 20, especially 2 to 12, carbon atoms, including a methoxycarbonylamino group. The aryloxycarbonylamino group preferably contains 7 to 30, particularly 7 to 20, especially 7 to 12 carbon atoms, including a phenyloxycarbonylamino group.

The sulfonylamino group preferably has 1 to 30, particularly 1 to 20, especially 1 to 12, carbon atoms, including methanesulfonylamino and benzenesulfonylamino groups. The sulfamoyl group preferably has up to 30, particularly up to 20, especially up to 12, carbon atoms, including sulfamoyl, methylsulfamoyl, dimethylsulfamoyl, and phenylsulfamoyl groups. The carbamoyl group preferably contains 1 to 30, particularly 1 to 20, especially 1 to 12, carbon atoms, including carbamoyl, methylcarbamoyl, diethylcarbamoyl, and phenylcarbamoyl groups.

The alkylthio group preferably has 1 to 30, particularly 1 to 20, especially 1 to 12, carbon atoms, including methylthio and ethylthio groups. The arylthio group preferably has 6 to 30, particularly 6 to 20, especially 6 to 12, carbon atoms, including a phenylthio group. The sulfonyl group preferably has 1 to 30, particularly 1 to 20, especially 1 to 12, carbon atoms, including mesyl and tosyl groups. The sulfinyl group preferably has 1 to 30, particularly 1 to 20, especially 1 to 12, carbon atoms, including methanesulfinyl and benzenesulfinyl groups.

The ureido group preferably has 1 to 30, particularly 1 to 20, especially 1 to 12, carbon atoms, including ureido, methylureido, and phenylureido groups. The phosphoric acid amido group preferably has 1 to 30, particularly 1 to 20, especially 1 to 12, carbon atoms, including a diethylphosphoric acid amido group and a phenylphosphoric acid amido group. The halogen atom includes fluorine, chlorine, bromine and iodine.

The heterocyclic group preferably contains 1 to 30 carbon atoms, particularly 1 to 12 carbon atoms. The hetero atom includes nitrogen, oxygen and sulfur. Examples of the heterocyclic group are imidazolyl, pyridyl, quinolyl, furyl, piperidyl, morpholino, benzoxazolyl, benzimidazolyl, benzothiazolyl, and thienyl groups. The silyl group preferably contains 3 to 40, particularly 3 to 30, especially 3 to 24, carbon atoms, including trimethylsilyl and triphenylsilyl groups.

These substituents can further have a substituent(s). Where they have two or more substituents, the substituents may be the same or different or, if possible, may be linked to form a ring.

It is desirable that $R_{2c}$, $R_{2d}$, $R_{2e}$, $R_{3c}$, $R_{3d}$, $R_{3f}$, $R_{4c}$, $R_{4d}$, and $R_{4f}$ each represent an alkyl group, an alkenyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or a heterocyclic group. It is more desirable that they individually represent an alkyl group, an alkenyl group, an aryl group, an amino group, an alkoxy group, an aryloxy group, a halogen atom or an aromatic heterocyclic group. It is the most desirable that they individually represent an alkyl group, an alkenyl group, an aryl group, an amino group, an alkoxy group, an aryloxy group or an aromatic heterocyclic group.

In formulae (II) to (IV), 2p, 2q, 2r, 3p, 3r, and 4r each represent an integer of from 0 to 4, preferably 0, 1, 2 or 3, still preferably 0, 1 or 2, particularly preferably 0 or 1. 3q, 4p, and 4q each represent an integer of from 0 to 3, preferably 0, 1, or 2, still preferably 0 or 1, particularly preferably 0.

Where 2p, 2q, 2r, 3p, 3q, 3r, 4p, 4q, or 4r is 2 or greater, two or more $R_{2c}$'s, $R_{2d}$'s, $R_{2e}$'s, $R_{3c}$'S, $R_{3d}$'s, $R_{3f}$'s, $R_{4c}$'s, $R_{4d}$'s or $R_{4f}$'s may be either the same or different and, if possible, may be connected together to form a ring.

In formulae (III) and (IV), $R_{3e}$ and $R_{4e}$ are independently a hydrogen atom or a substituent. The substituent includes an alkyl group, an alkenyl group, an alkynyl group, an aryl group, an acyl group, an alkoxycarbonyl group, an aryloxycarbonyl group, a sulfamoyl group, a carbamoyl group, a sulfonyl group, a sulfinyl group, a phosphoric acid amido group, a heterocyclic group, and a silyl group.

The alkyl group preferably has 1 to 30, particularly 1 to 20, especially 1 to 10, carbon atoms, including methyl, ethyl, isopropyl, t-butyl, n-octyl, n-decyl, n-hexadecyl, cyclopropyl, cyclopentyl and cyclohexyl groups. The alkenyl group preferably contains 2 to 30, particularly 2 to 20, especially 2 to 10, carbon atoms, including vinyl, allyl, 2-butenyl, and 3-pentenyl groups. The alkynyl group preferably has 2 to 30, particularly 2 to 20, especially 2 to 10, carbon atoms, including propargyl and 3-pentynyl groups.

The aryl group preferably contains 6 to 30 carbon atoms, particularly 6 to 20 carbon atoms, especially 6 to 12 carbon atoms and includes phenyl, p-methylphenyl, and naphthyl groups. The acyl group preferably contains 1 to 30, particularly 1 to 20, especially 2 to 12, carbon atoms, including acetyl, benzoyl, formyl, and pivaloyl groups. The alkoxycarbonyl group preferably has 2 to 30, particularly 2 to 20, especially 2 to 12, carbon atoms, including methoxycarbonyl and ethoxycarbonyl groups. The aryloxycarbonyl group preferably has 7 to 30, particularly 7 to 20, especially 7 to 12, carbon atoms, including a phenyloxycarbonyl group.

The sulfamoyl group preferably has up to 30, particularly up to 20, especially up to 12, carbon atoms, including sulfamoyl, methylsulfamoyl, dimethylsulfamoyl, and phenylsulfamoyl groups. The carbamoyl group preferably contains 1 to 30, particularly 1 to 20, especially 1 to 12, carbon atoms, including carbamoyl, methylcarbamoyl, diethylcarbamoyl, and phenylcarbamoyl groups. The sulfonyl group preferably has 1 to 30, particularly 1 to 20, especially 1 to 12, carbon atoms, including mesyl and tosyl groups.

The sulfinyl group preferably has 1 to 30, particularly 1 to 20, especially 1 to 12, carbon atoms, including methanesulfinyl and benzenesulfinyl groups. The phosphoric acid amido group preferably has 1 to 30, particularly 1 to 20, especially 1 to 12, carbon atoms, including a diethylphosphoric acid amido group and a phenylphosphoric acid amido group.

The heterocyclic group preferably contains 1 to 30 carbon atoms, particularly 1 to 12 carbon atoms. The hetero atom includes nitrogen, oxygen and sulfur. Examples of the heterocyclic group are imidazolyl, pyridyl, quinolyl, furyl, piperidyl, morpholino, benzoxazolyl, benzimidazolyl, benzothiazolyl, and thienyl groups. The silyl group preferably contains 3 to 40, particularly 3 to 30, especially 3 to 24, carbon atoms, including trimethylsilyl and triphenylsilyl groups.

These substituents can further have a substituent(s). Where they have two or more substituents, the substituents may be the same or different or, if possible, maybe connected together to form a ring.

It is desirable that $R_{3e}$ and $R_{4e}$ be individually a hydrogen atom, an alkyl group, an alkenyl group, an aryl group, an acyl group, a sulfamoyl group, a carbamoyl group, a sulfonyl group or a heterocyclic group. It is more desirable that they be each an alkyl group, an aryl group or an aromatic heterocyclic group. It is particularly preferred that they be each an aryl group or an aromatic heterocyclic group. An aryl group is the most preferred.

In formulae (II) through (IV), $L_2$, $L_3$, and $L_4$ each represent a single bond or a divalent linking group. The divalent linking group may be straight, branched or cyclic. Examples of the linking group are —O—, —S—, —SO—, —SO$_2$—, —N(R$_1$)— (wherein R$_1$ represents a hydrogen atom or a substituent, the substituent including those enumerated above as the substituents represented by $R_{2c}$, $R_{2d}$, $R_{2e}$, $R_{3c}$, $R_{3d}$, $R_{3f}$, $R_{4c}$, $R_{4d}$, and $R_{4f}$; $R_1$ preferably represents a hydrogen atom, an aliphatic hydrocarbon group, an aryl group or a heterocyclic group, particularly a hydrogen atom, an alkyl group, an aryl group or a heterocyclic group), —N=, —N=N—, —CO—, —SiR$_2$(R$_3$)— (wherein R$_2$ and R$_3$ each represent a hydrogen atom, an aliphatic hydrocarbon group, an aryl group or a heterocyclic group, preferably an aliphatic hydrocarbon group, an aryl group or a heterocyclic group, still preferably an aliphatic hydrocarbon group or an aryl group, especially an alkyl group, an alkenyl group or an aryl group), a divalent aliphatic hydrocarbon group (e.g., an alkylene group, an alkenylene group, an alkynylene group or a combination thereof), an arylene group, a divalent heterocyclic group, and combinations thereof. These divalent linking groups may have a substituent(s) selected from, for example, the substituents enumerated above as the substituents represented by $R_{2c}$.

More specifically, $L_2$ preferably represents a single bond or a divalent linking group containing an alkylene group, an alkenylene group, an alkynylene group, an arylene group or an aromatic heterocyclic group. It is still preferred that $L_2$ be a single bond, an arylene group or a divalent aromatic heterocyclic group. It is particularly preferred that $L_2$ be a single bond or an arylene group, especially a single bond, a phenylene group or a biphenylene group. A phenylene group is the most preferred. Specific examples of the preferred divalent linking group as $L_2$ are shown below.

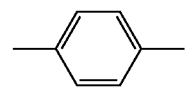

(L$_2$-1)

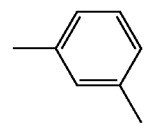

(L$_2$-2)

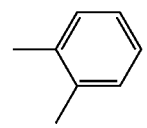

(L$_2$-3)

(L$_2$-4)

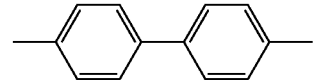

(L$_2$-5)

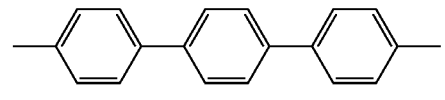

(L$_2$-6)

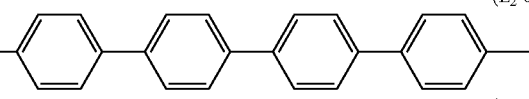

(L$_2$-7)

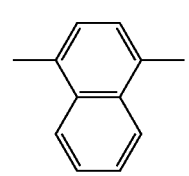

(L$_2$-8)

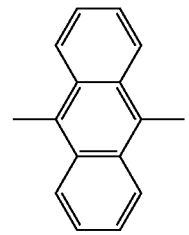

(L$_2$-9)

-continued

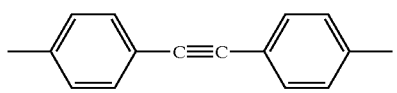 (L₂-10)

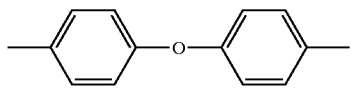 (L₂-11)

—CH₂— (L₂-12)

—CONHCH₂CH₂— (L₂-13)

—COOCH₂CH₂— (L₂-14)

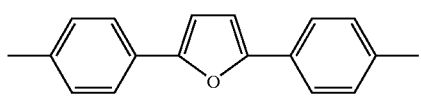 (L₂-15)

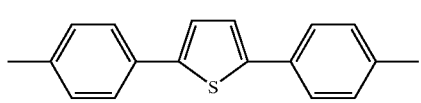 (L₂-16)

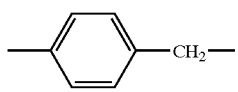 (L₂-17)

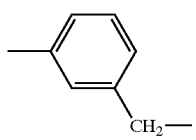 (L₂-18)

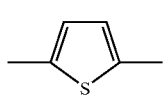 (L₂-19)

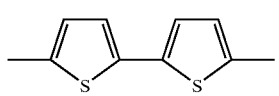 (L₂-20)

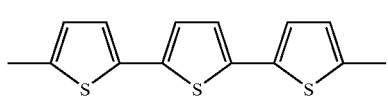 (L₂-21)

L₃ preferably represents a single bond or a divalent linking group selected from —O—, —N(R₁)— (wherein R₁ is as defined above), —CO—, an alkylene group, an alkenylene group, an alkynylene group, an arylene group, a divalent aromatic heterocyclic group, and combinations thereof. It is still preferred for L₃ to represent a single bond, an arylene group or a divalent aromatic heterocyclic group, particularly a single bond or an arylene group. A single bond is the most preferred. Specific examples of the preferred divalent linking group as L₃ are shown below.

—O— (L₃-1)

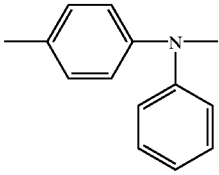 (L₃-2)

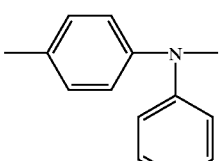 (L₃-3)

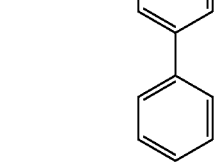 (L₃-4)

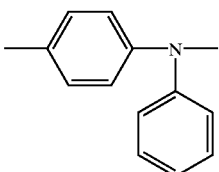 (L₃-5)

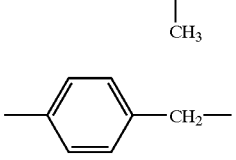 (L₃-6)

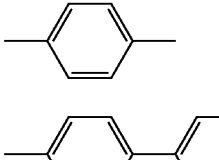 (L₃-7)

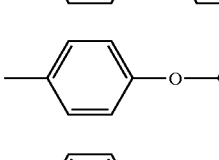 (L₃-8)

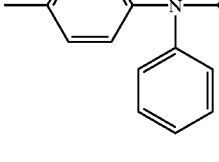 (L₃-9)

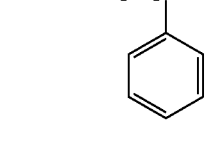 (L₃-10)

(L₃-11)
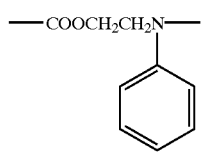

(L₃-12)
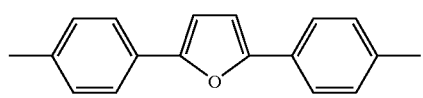

(L₃-13)
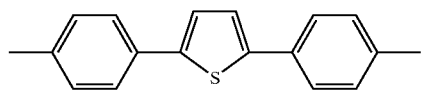

(L₃-14)
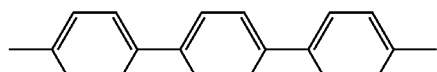

$L_4$ preferably represents a single bond or a divalent linking group selected from —O—, —N($R_1$)— (wherein $R_1$ is as defined above), —CO—, an alkylene group, an alkenylene group, an alkynylene group, an arylene group, a divalent aromatic heterocyclic group, and combinations thereof. It is still preferred for $L_4$ to represent a single bond, —O—, —N($R_1$)—, —CO—, an alkylene group, an alkenylene group, an arylene group, a divalent aromatic heterocyclic group, or a combination thereof. Specific examples of the preferred divalent linking group as $L_4$ are shown below.

(L₄-1)
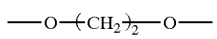

(L₄-2)
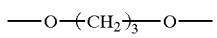

(L₄-3)
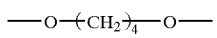

(L₄-4)
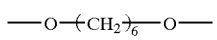

(L₄-5)
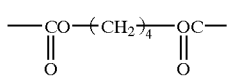

(L₄-6)
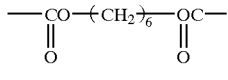

(L₄-7)
—CH=CH—

(L₄-8)
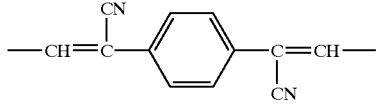

(L₄-9)
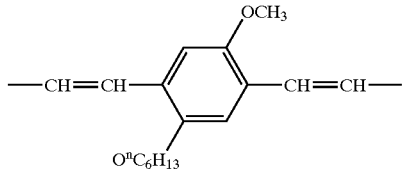

(L₄-10)
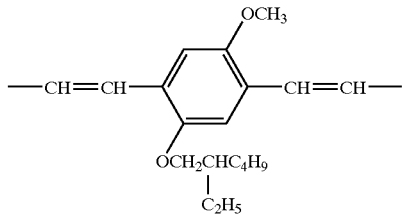

(L₄-11)
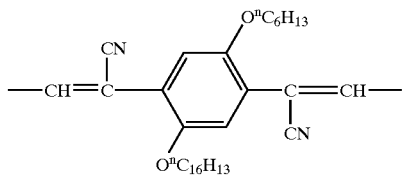

(L₄-12)
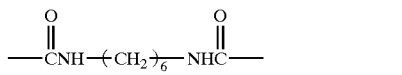

(L₄-13)
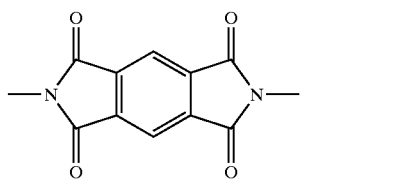

(L₄-14)
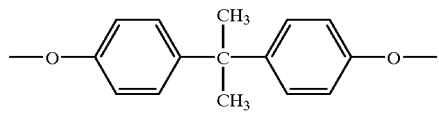

(L₄-15)
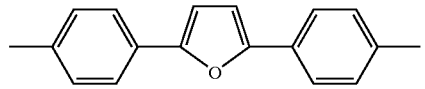

(L₄-16)
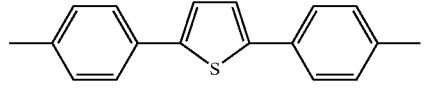

(L₄-17)
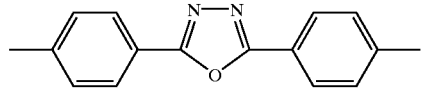

(L₄-18)
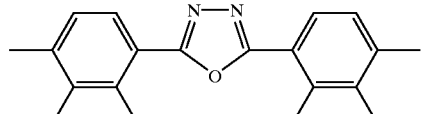

(L₄-19)
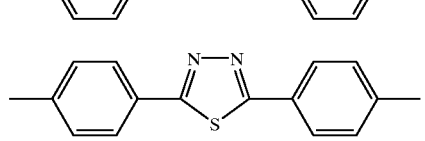

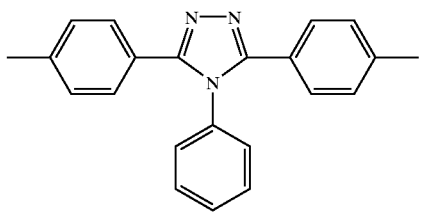
(L4-20)

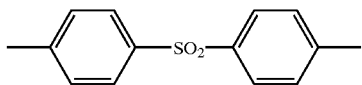
(L4-21)

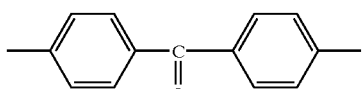
(L4-22)

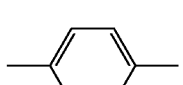
(L4-23)

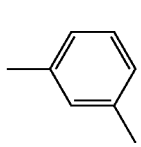
(L4-24)

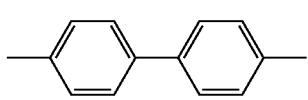
(L4-25)

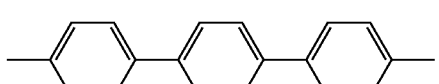
(L4-26)

In formulae (II) and (III), $R_{21}$ and $R_{31}$ each represent a hydrogen atom, an alkyl group or an aryl group. The alkyl group preferably has 1 to 30, particularly 1 to 20, especially 1 to 10, carbon atoms, including methyl, ethyl, isopropyl, t-butyl, n-octyl, n-decyl, n-hexadecyl, cyclopropyl, cyclopentyl and cyclohexyl groups. The aryl group preferably has 6 to 30, particularly 6 to 20, especially 6 to 12, carbon atoms, including phenyl, p-methylphenyl, and naphthyl groups. The alkyl group or aryl group as $R_{21}$ and $R_{31}$ may have a substituent (s), such as those enumerated above as $R_{2c}$.

It is preferred that $R_{21}$ and $R_{31}$ each represent a hydrogen atom or an alkyl group. It is still preferred that they each represent a hydrogen atom or a lower alkyl group (particularly a methyl group). A hydrogen atom is the most preferred as $R_{21}$ and $R_{31}$.

In formulae (II) through (IV), $m_2$, $m_3$, and $m_4$ each represent an integer of 1 or greater, preferably 6 to 100,000, still preferably 10 to 10,000, particularly preferably 10 to 5,000.

Of the preferred polymers containing at least one repeating unit of formula (II), still preferred are those having at least one repeating unit represented by formula (II-A):

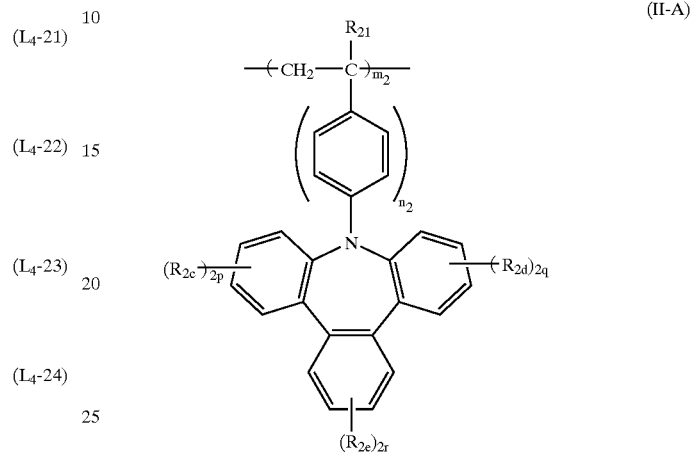

(II-A)

wherein $R_{2c}$, $R_{2d}$, $R_{2e}$, 2p, 2q, 2r, $R_{21}$, and $m_2$ are as defined above; and $n_2$ represents an integer of from 0 to 4.

In formula (II-A), $n_2$ is preferably 0, 1, 2 or 3, still preferably 0, 1 or 2, particularly preferably 0 or 1, the most preferably 1. The preference for $R_{2c}$, $R_{2d}$, $R_{2e}$, 2p, 2q, 2r, $R_{21}$, and $m_2$ as described with respect to formula (II) applies to formula (II-A).

Polymer A may be a homopolymer or a copolymer comprising other repeating units. The copolymer can be a random copolymer or a block copolymer.

While subject to variation depending on the substituents, the number average molecular weight (Mn) of polymer A preferably ranges from 2,000 to 500,000, still preferably 3,000 to 300,000, particularly preferably 3,000 to 200,000. The weight average molecular weight (Mw), also varying depending on the substituents, preferably ranges from 2,000 to 1,500,000, still preferably 3,000 to 1,000,000, particularly preferably 3,000 to 500,000.

Polymer A may contain, in the molecule thereof, a skeleton having a hole-transporting function, an electron-transporting function or a light-emitting function.

Specific examples of polymer A are shown below for illustrative purposes only but not for limitation.

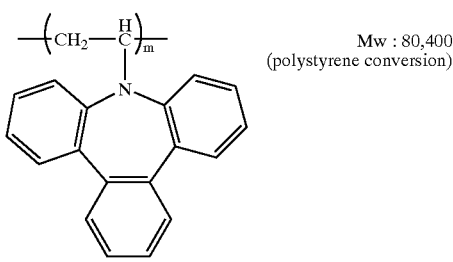
Mw : 80,400
(polystyrene conversion)

1

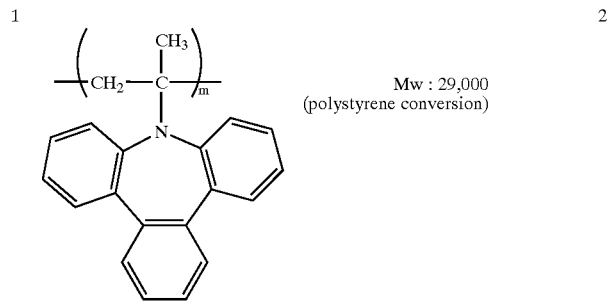
Mw : 29,000
(polystyrene conversion)

2

-continued
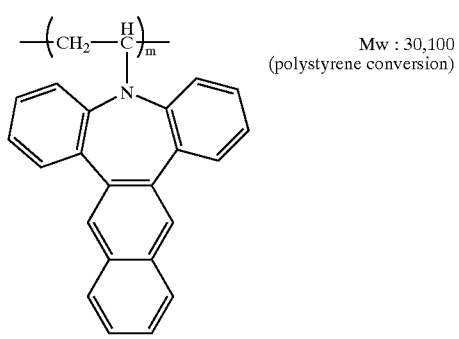
3
Mw : 30,100
(polystyrene conversion)
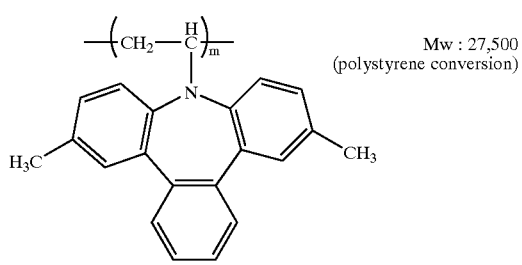
4
Mw : 27,500
(polystyrene conversion)
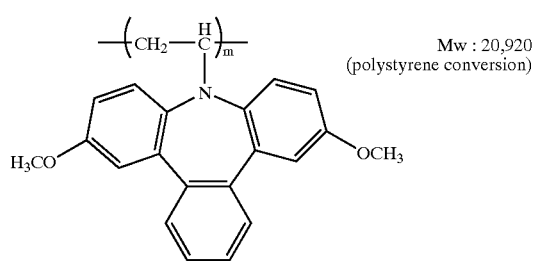
5
Mw : 20,920
(polystyrene conversion)
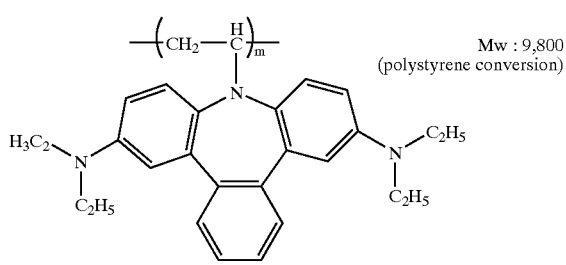
6
Mw : 9,800
(polystyrene conversion)
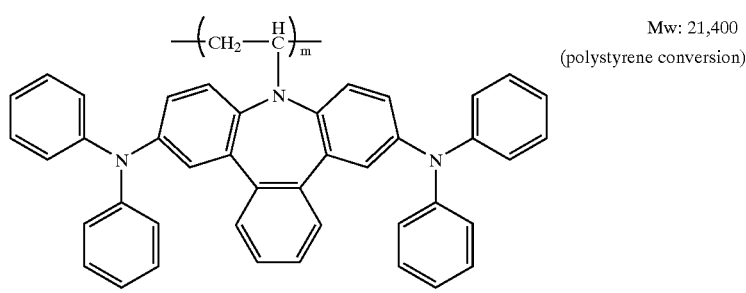
7
Mw: 21,400
(polystyrene conversion)
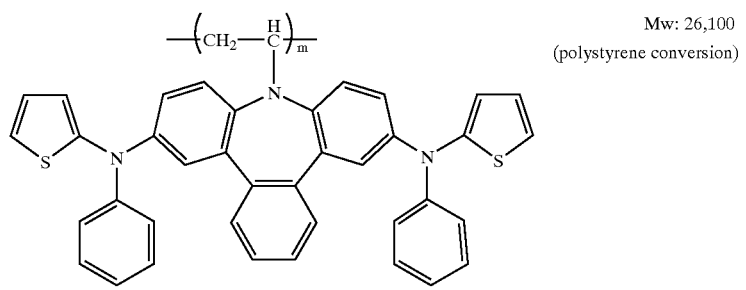
8
Mw: 26,100
(polystyrene conversion)
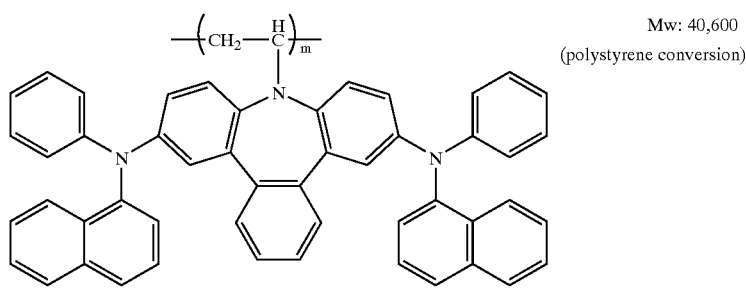
9
Mw: 40,600
(polystyrene conversion)

-continued
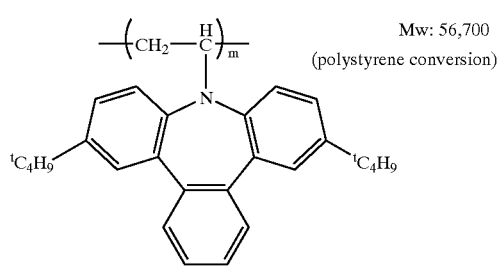 10
Mw: 56,700
(polystyrene conversion)
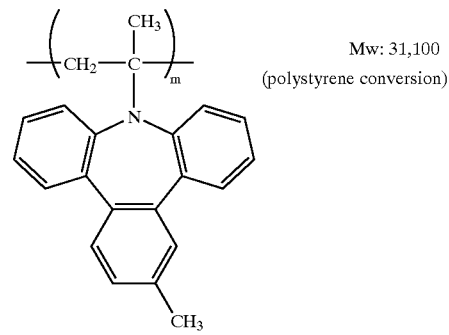 11
Mw: 31,100
(polystyrene conversion)
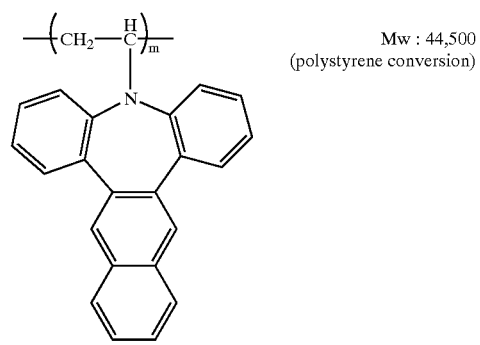 12
Mw : 44,500
(polystyrene conversion)
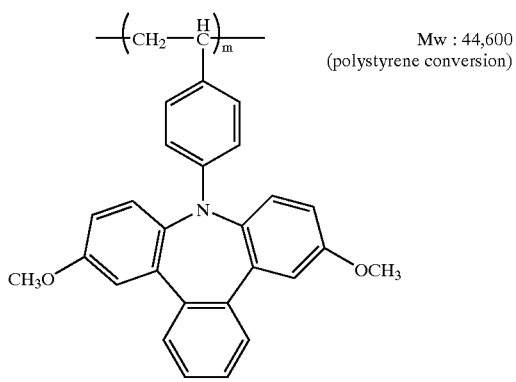 13
Mw : 44,600
(polystyrene conversion)
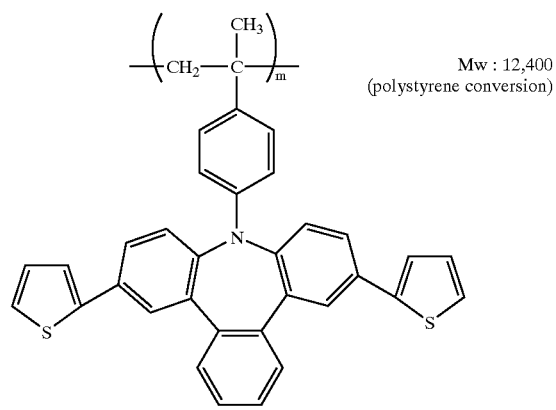 14
Mw : 12,400
(polystyrene conversion)
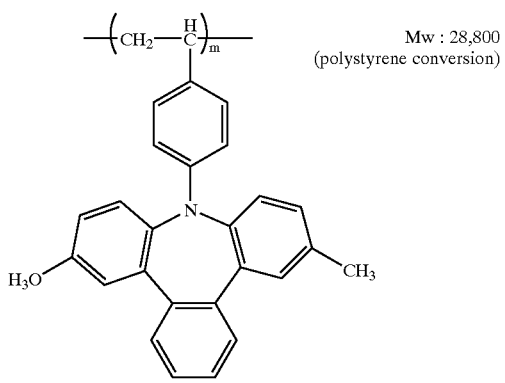 15
Mw : 28,800
(polystyrene conversion)
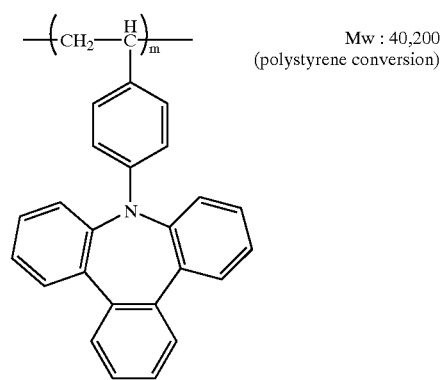 16
Mw : 40,200
(polystyrene conversion)
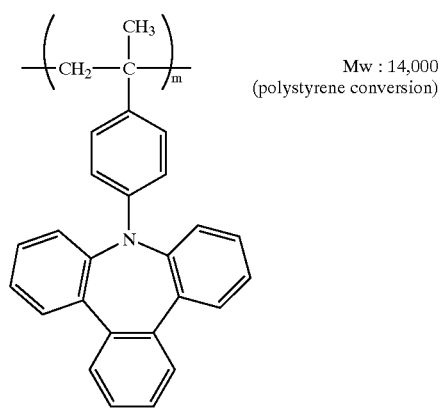 17
Mw : 14,000
(polystyrene conversion)

-continued
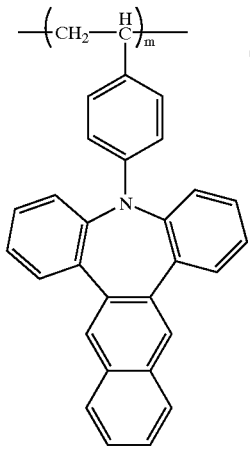
18
Mw : 22,900
(polystyrene conversion)
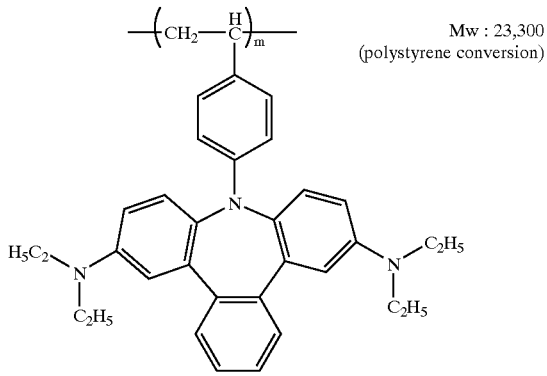
19
Mw : 23,300
(polystyrene conversion)
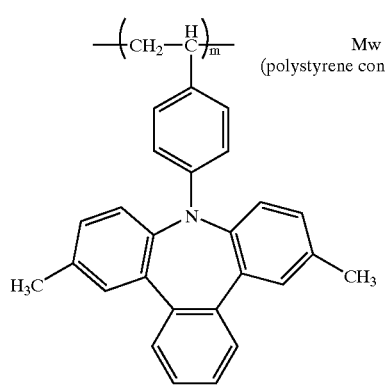
20
Mw : 39,600
(polystyrene conversion)
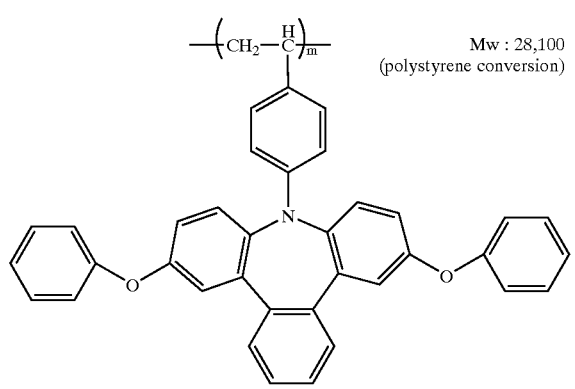
21
Mw : 28,100
(polystyrene conversion)
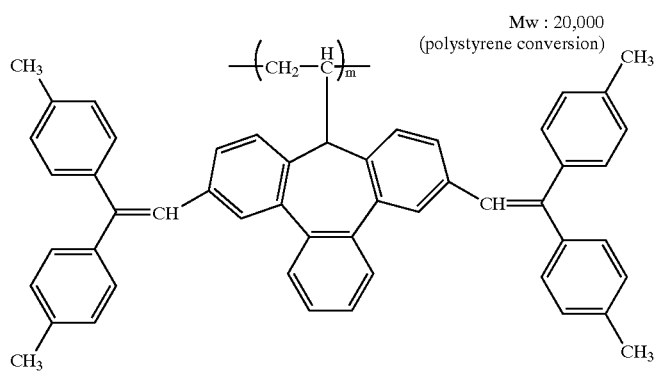
22
Mw : 20,000
(polystyrene conversion)
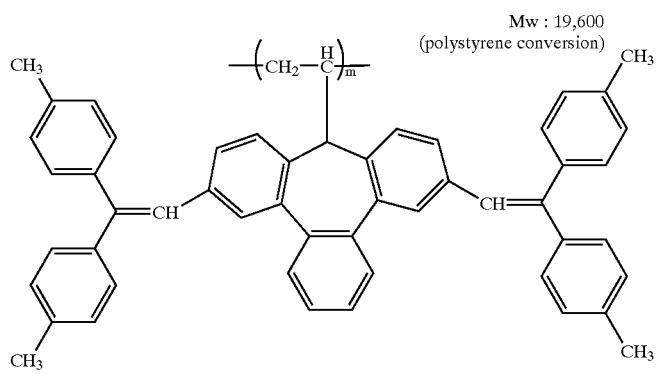
23
Mw : 19,600
(polystyrene conversion)

-continued
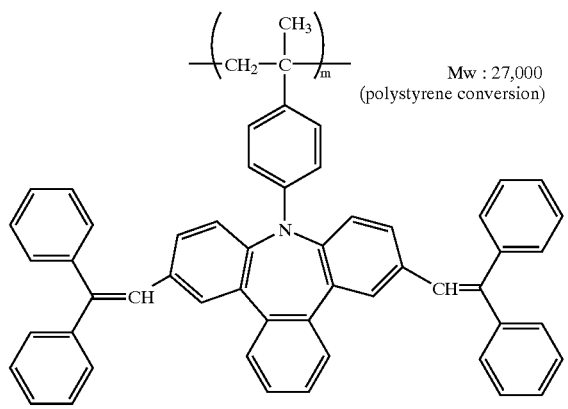
24
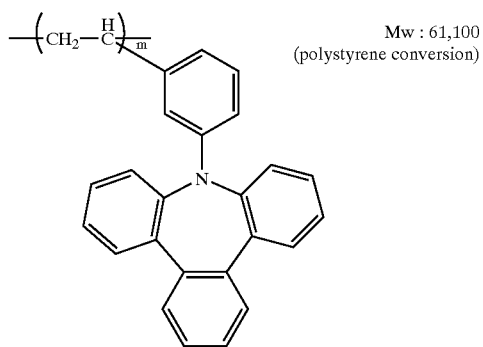
25
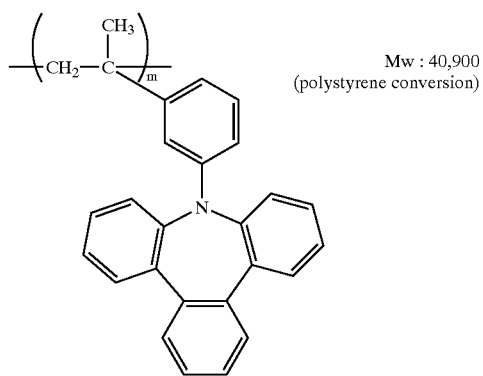
26 27
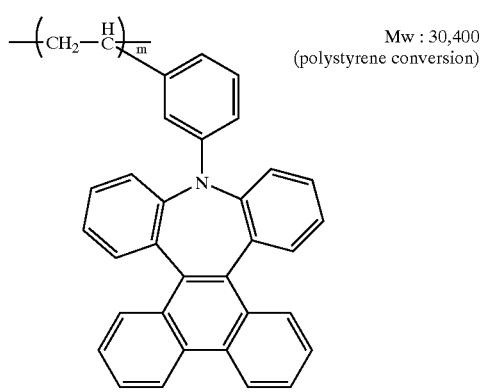
28 29

-continued
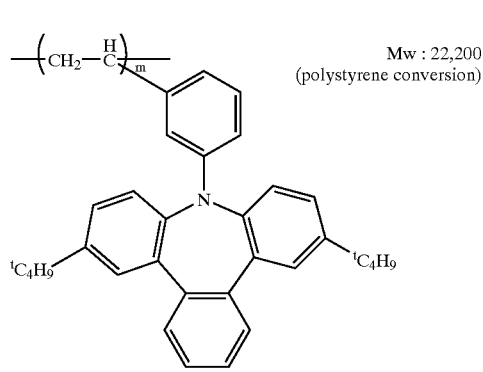
30
Mw : 22,200
(polystyrene conversion)
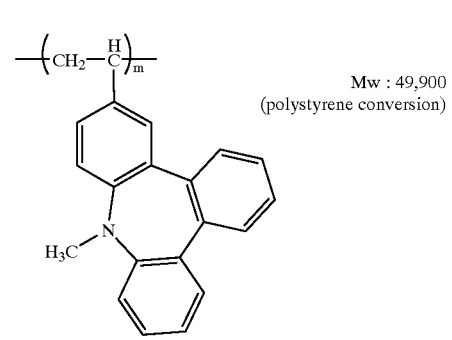
31
Mw : 49,900
(polystyrene conversion)
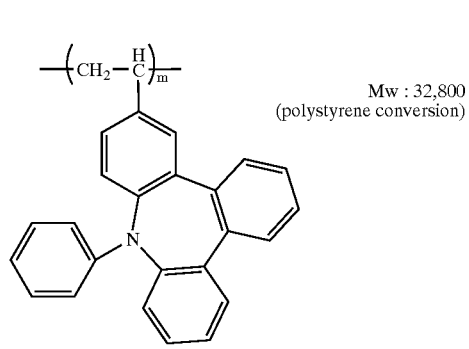
32
Mw : 32,800
(polystyrene conversion)
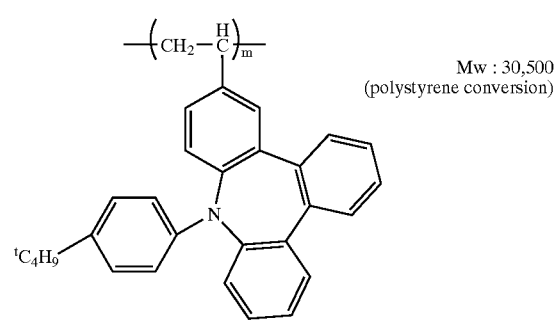
33
Mw : 30,500
(polystyrene conversion)
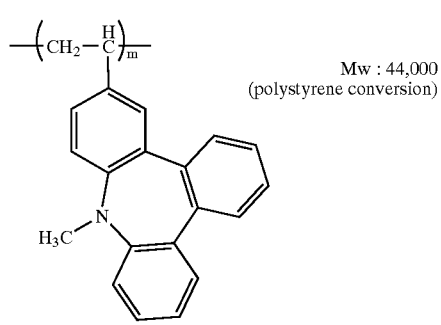
34
Mw : 44,000
(polystyrene conversion)
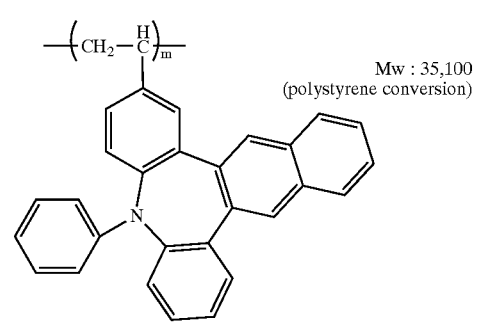
35
Mw : 35,100
(polystyrene conversion)
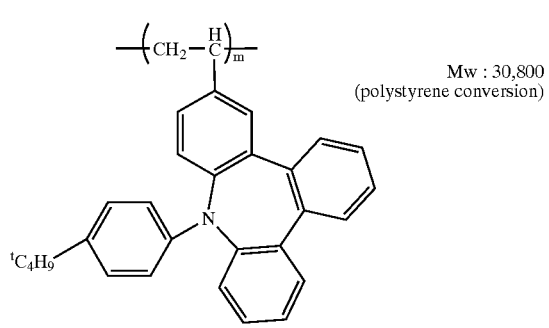
36
Mw : 30,800
(polystyrene conversion)

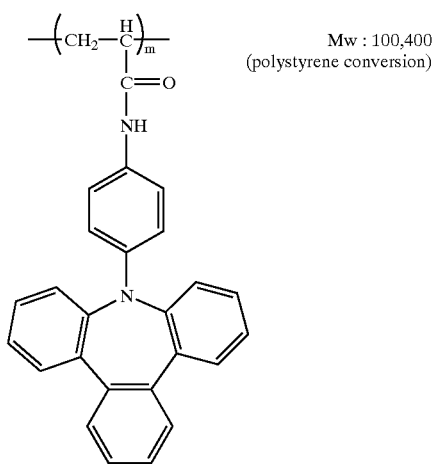
37
Mw : 100,400
(polystyrene conversion)
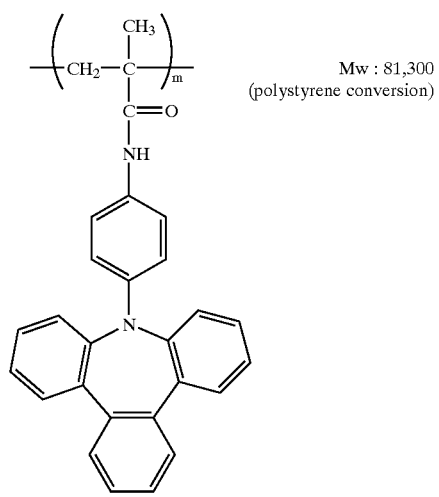
38
Mw : 81,300
(polystyrene conversion)
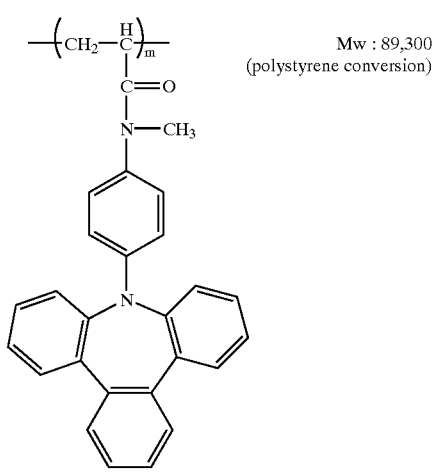
39
Mw : 89,300
(polystyrene conversion)
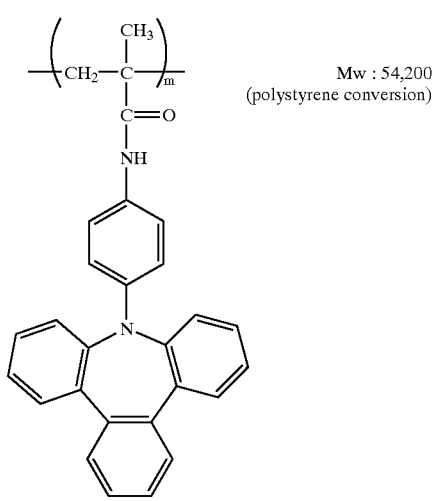
40
Mw : 54,200
(polystyrene conversion)
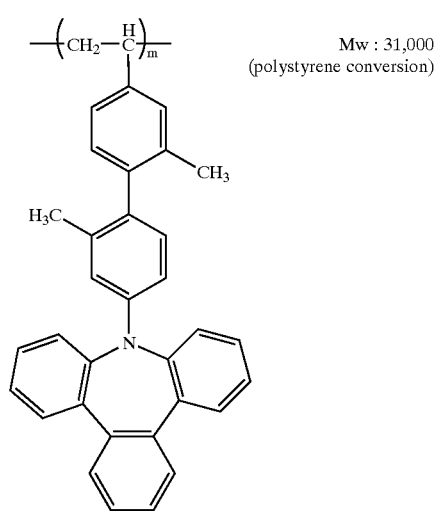
41
Mw : 31,000
(polystyrene conversion)

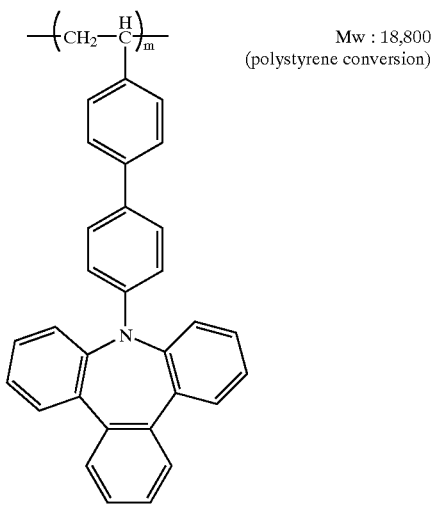
42
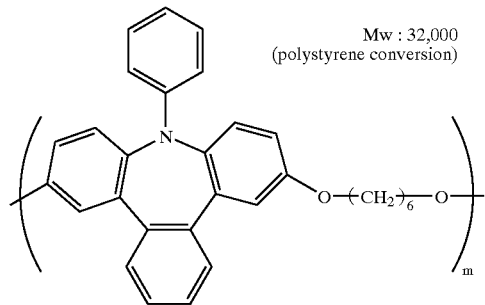
43
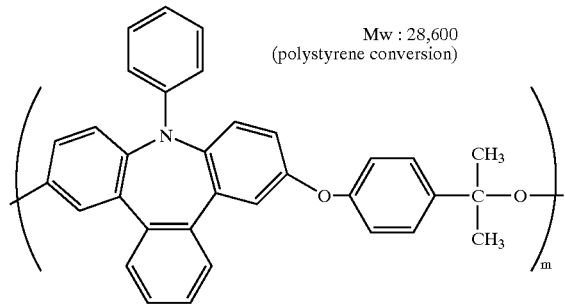
44
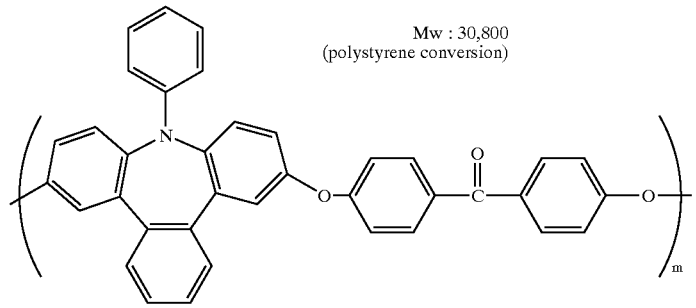
45

-continued
46
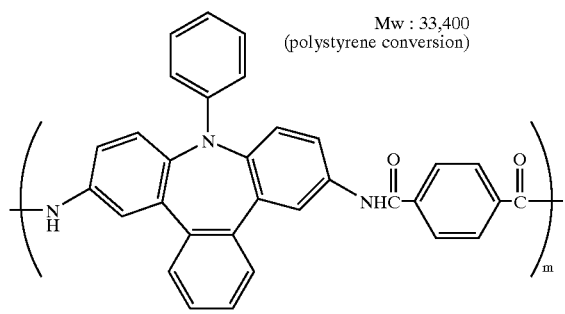
47
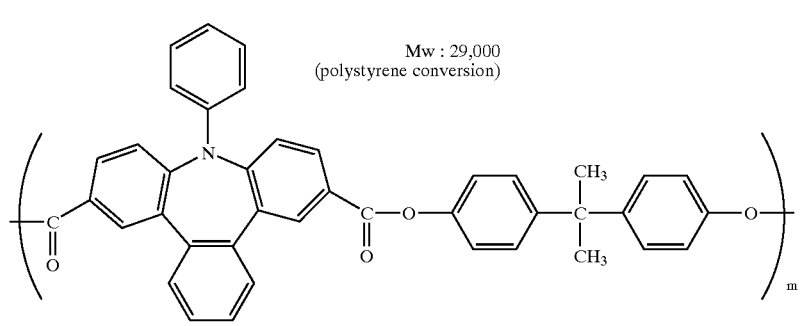
48
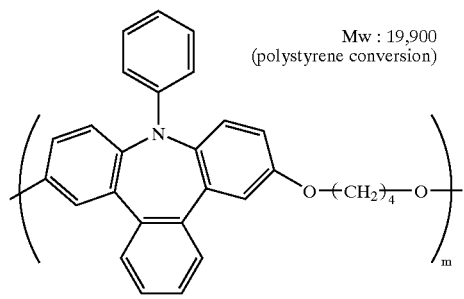
49
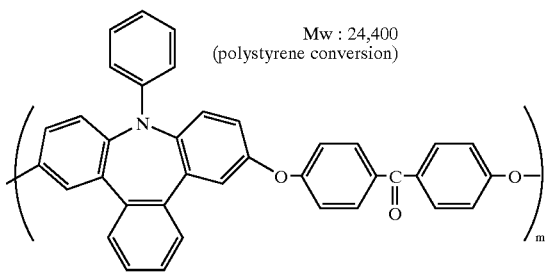
50
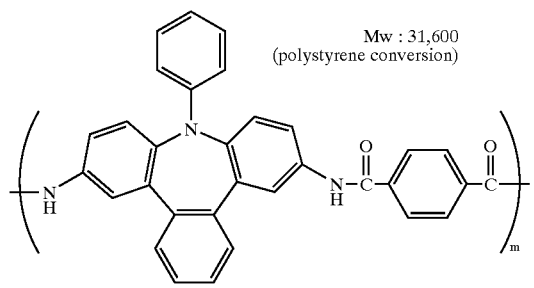
51
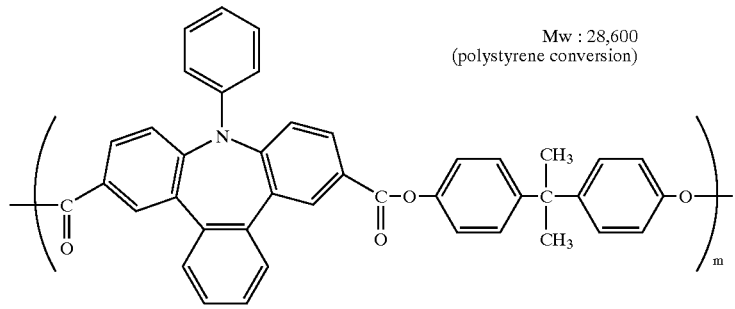

52
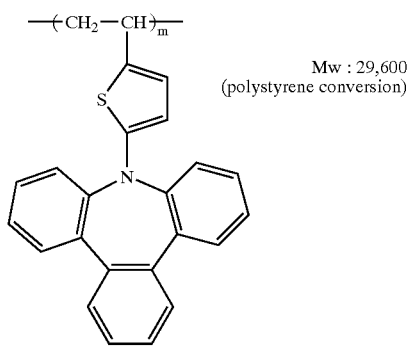
Mw : 29,600
(polystyrene conversion)
53
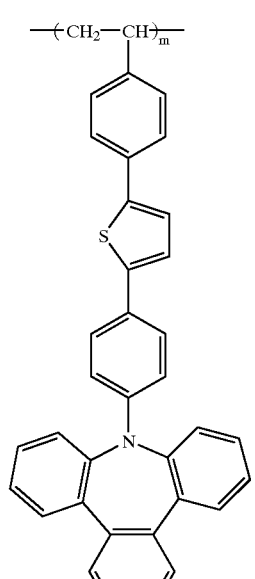
Mw : 26,300
(polystyrene conversion)
54
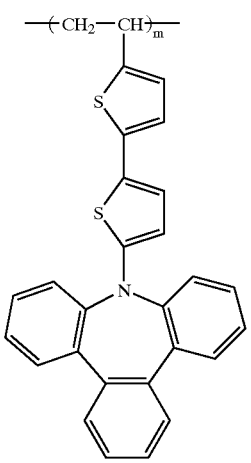
Mw : 22,800
(polystyrene conversion)
55
Mw : 22,900
(polystyrene conversion)
n : n=50 : 50 (weight ratio)
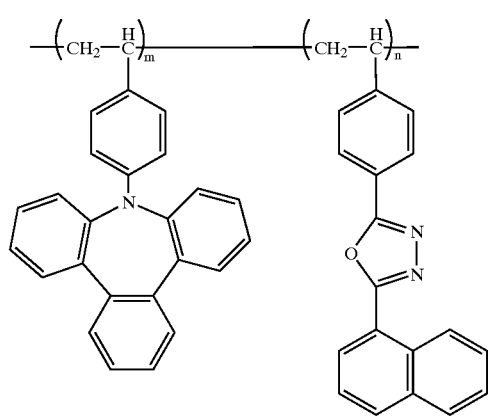

-continued
56
Mw : 19,000 (polystyrene conversion)
m : n = 95 : 5 (weight ratio)
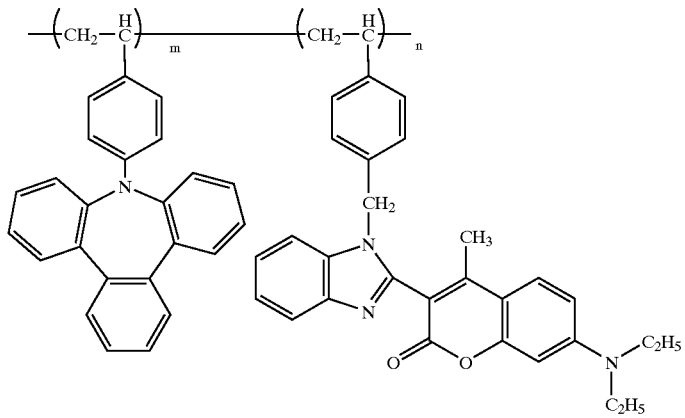
57
Mw : 8,600 (polystyrene conversion)
m:n = 99:1 (weight ratio)
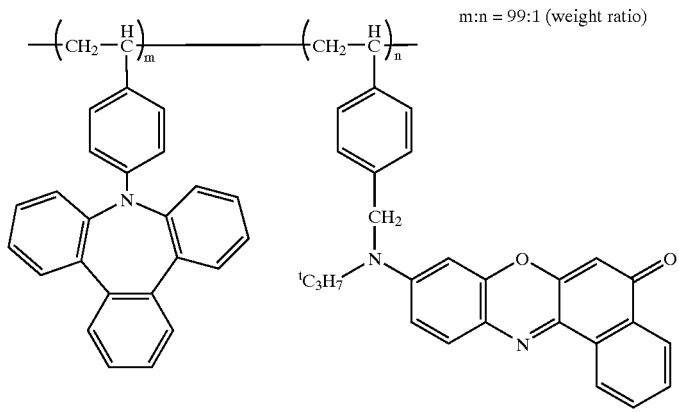
58
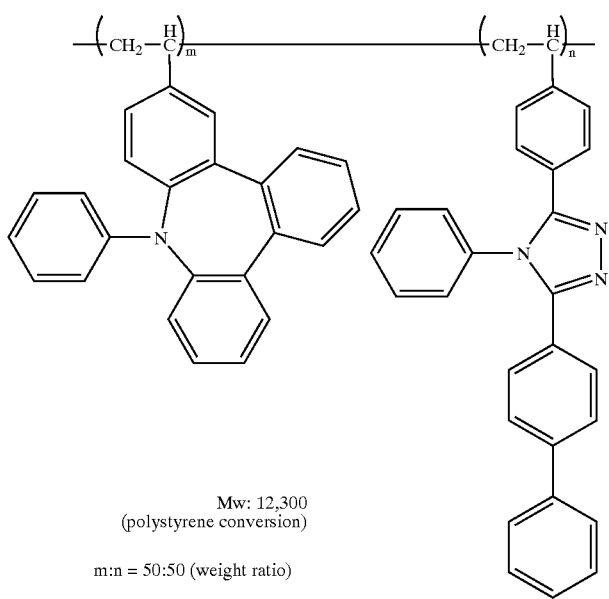
Mw: 12,300 (polystyrene conversion)
m:n = 50:50 (weight ratio)

-continued
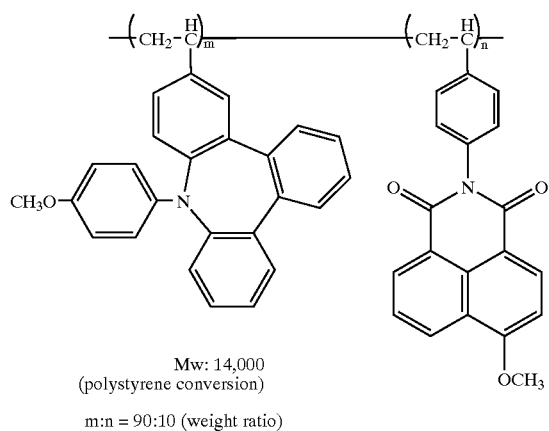
59
Mw: 14,000
(polystyrene conversion)
m:n = 90:10 (weight ratio)
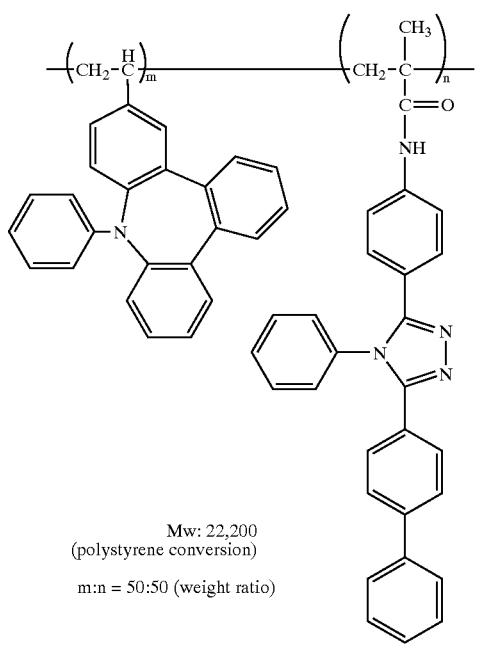
60
Mw: 22,200
(polystyrene conversion)
m:n = 50:50 (weight ratio)
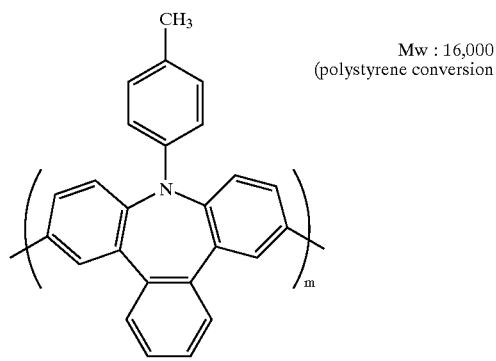
61
Mw : 16,000
(polystyrene conversion
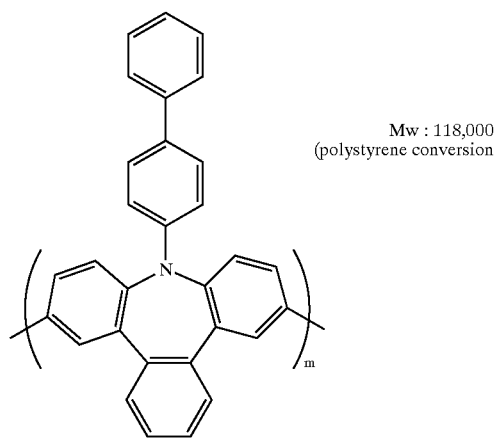
62
Mw : 118,000
(polystyrene conversion
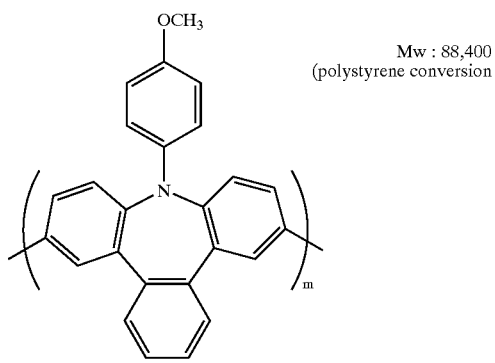
63
Mw : 88,400
(polystyrene conversion 64
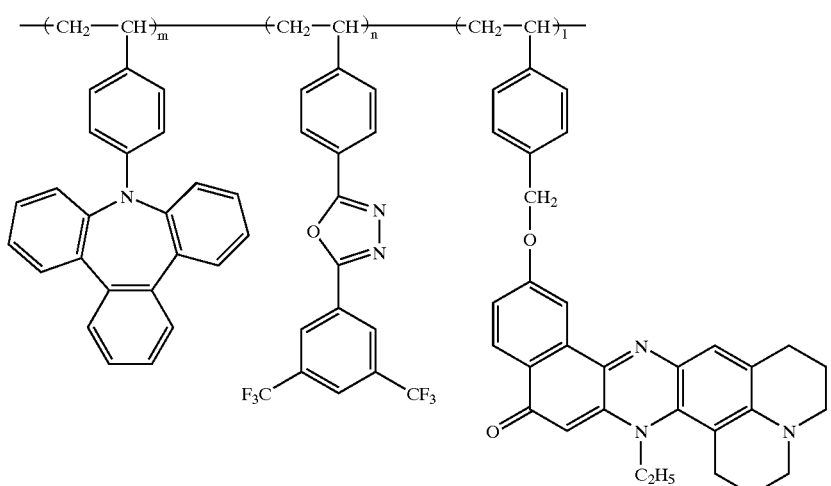
Mw : 20,600
(polystyrene conversion)
m:n:l = 48:48:4 (weight ratio)
65
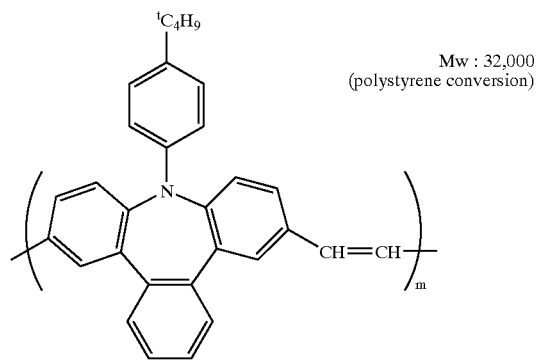
Mw : 32,000
(polystyrene conversion)
66
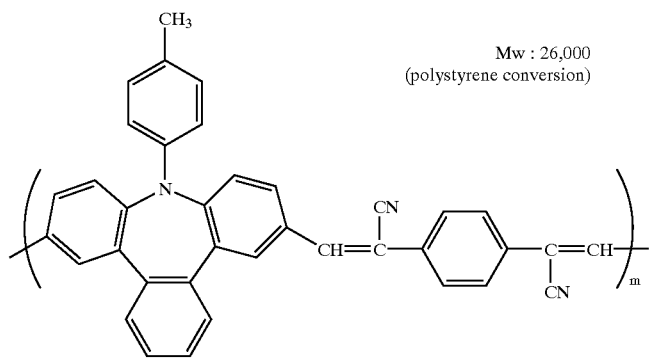
Mw : 26,000
(polystyrene conversion)

-continued
67
Mw : 30,600
(polystyrene conversion)
68
Mw : 22,400
(polystyrene conversion)
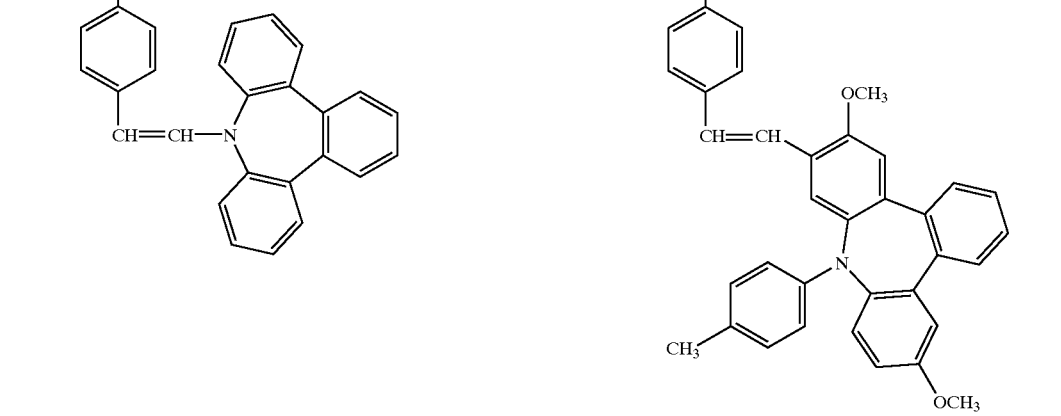
56
Mw: 19,000
(polystyrene conversion
m:n = 95:5 (weight ratio)
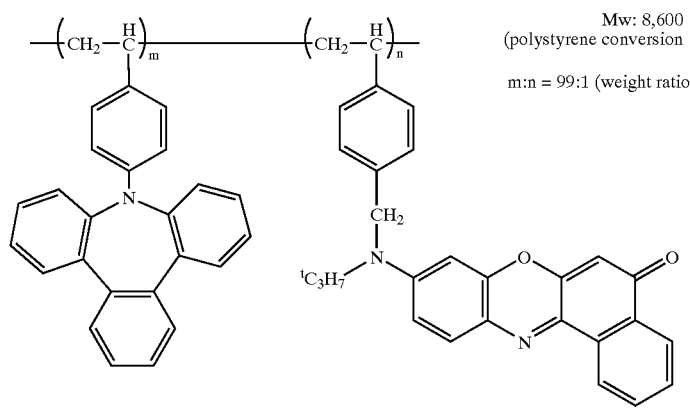
57
Mw: 8,600
(polystyrene conversion
m:n = 99:1 (weight ratio)

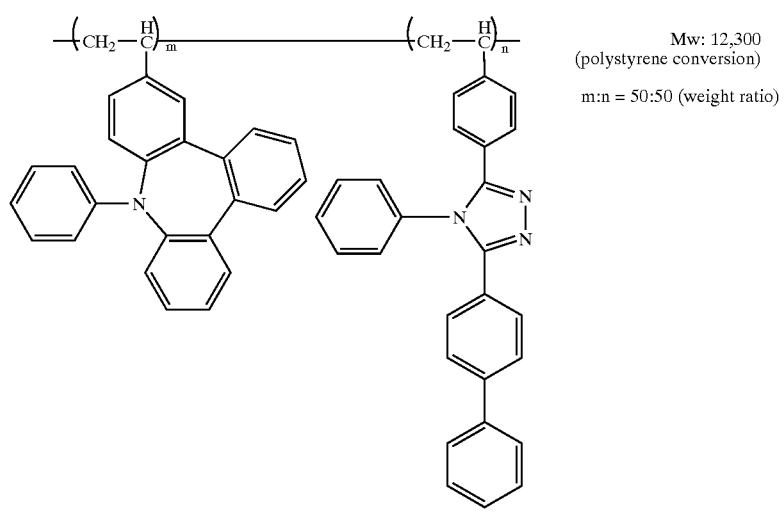
Mw: 12,300 (polystyrene conversion)
m:n = 50:50 (weight ratio)
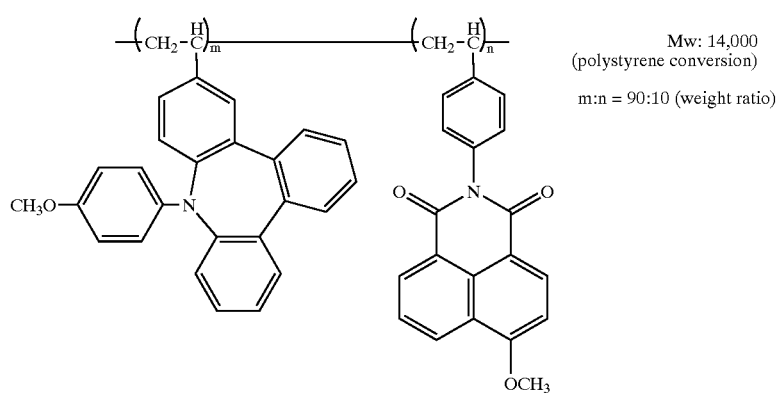
Mw: 14,000 (polystyrene conversion)
m:n = 90:10 (weight ratio)
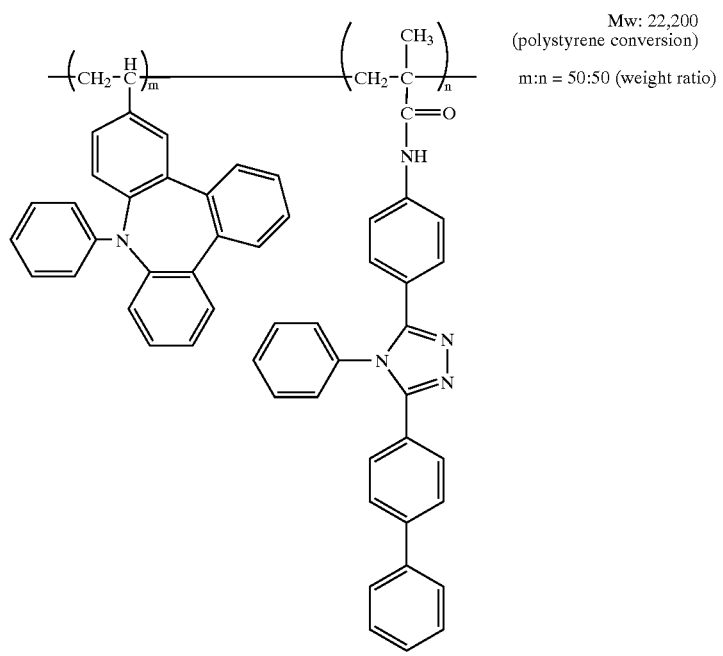
Mw: 22,200 (polystyrene conversion)
m:n = 50:50 (weight ratio)

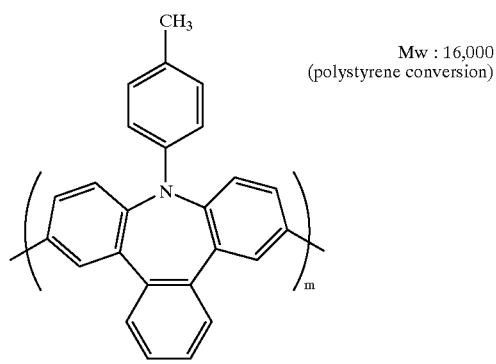
Mw : 16,000
(polystyrene conversion)
62
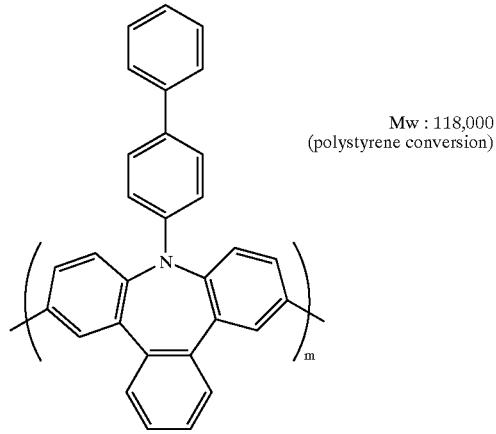
Mw : 118,000
(polystyrene conversion)
63
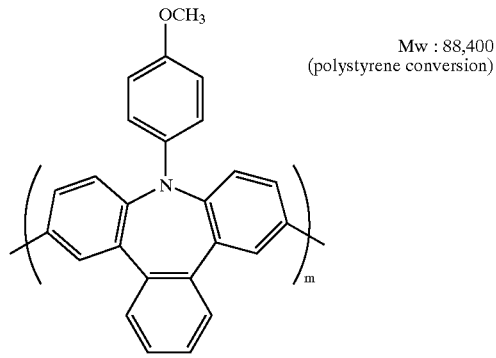
Mw : 88,400
(polystyrene conversion)
64
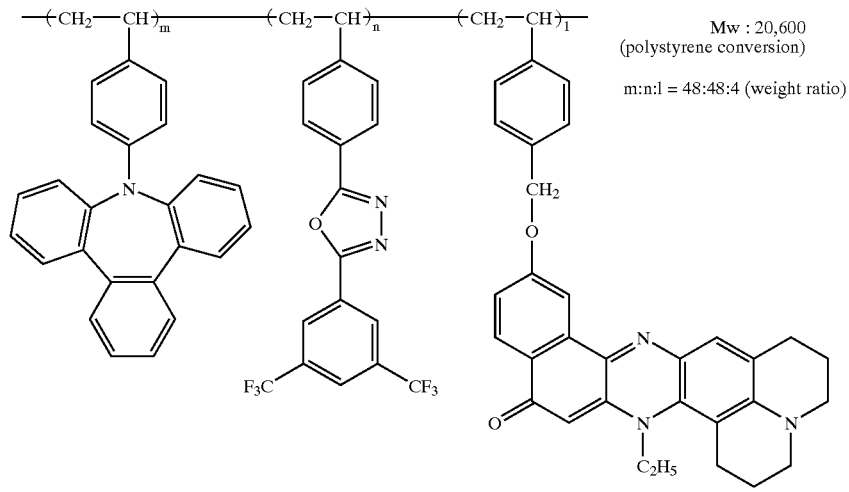
Mw : 20,600
(polystyrene conversion)
m:n:l = 48:48:4 (weight ratio)

65

Mw : 32,000
(polystyrene conversion)

66

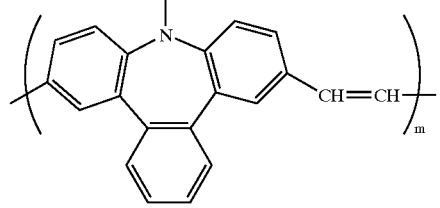

Mw: 26,000
(polystyrene conversion)

67

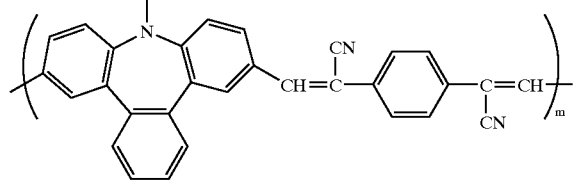

Mw: 30,600
(polystyrene conversion)

68

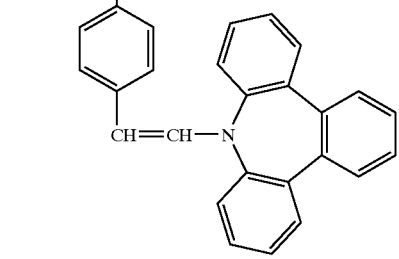

Mw: 22,400
(polystyrene conversion)

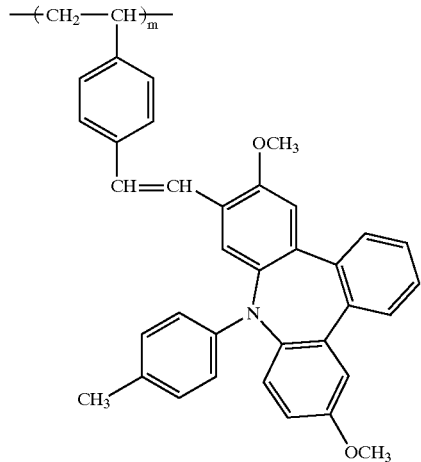

Polymer A is prepared by, for example, radical polymerization, ionic polymerization or oxidative polymerization, preferably radical polymerization. Initiators used in radical polymerization include azo compounds and peroxides. Preferred initiators include azobisisobutyronitrile, azobisisobutyric acid diester derivatives, and dibenzoyl peroxide.

Polymerization solvents include, for example, aromatic hydrocarbons (e.g., benzene and toluene), halogenated hydrocarbons (e.g., dichloroethane and chloroform),ethers (e.g., tetrahydrofuran and dioxane), amides (e.g., dimethylformamide and dimethylacetamide), esters (e.g., ethyl acetate), alcohols (e.g., methanol), and ketones (e.g., acetone and cyclohexanone) Appropriate selection of a solvent makes it possible to carry out solution polymerization in a homogeneous system or precipitation polymerization in a heterogeneous system in which the produced polymer precipitates.

Synthesis Examples for polymer A are shown below.

Synthesis of Polymer 16

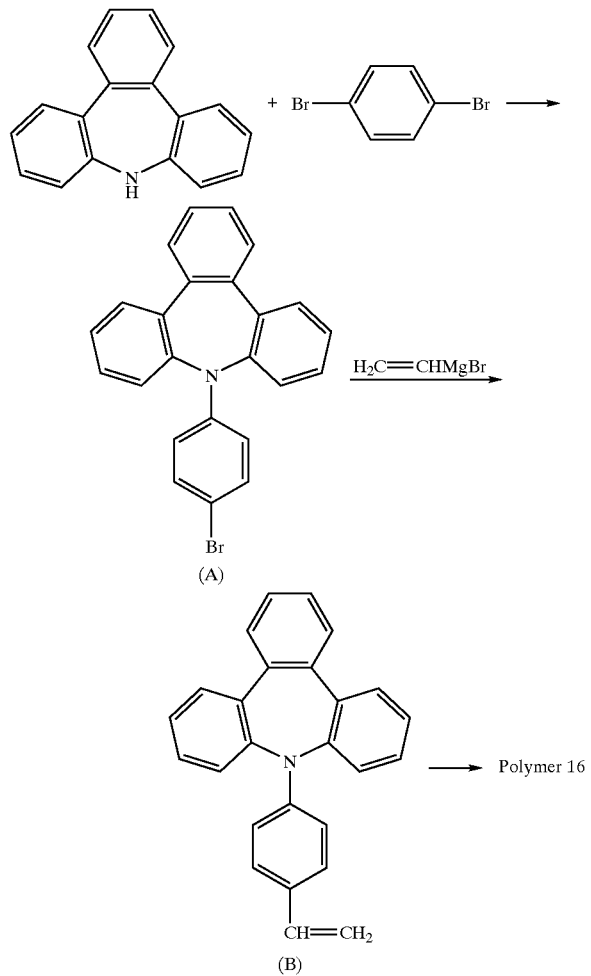

A mixture of 9.2 g (38 mmol) of 9H-tribenz[b,d,f]azepine (synthesized in accordance with *J. Org. Chem.*, vol. 56, p. 3906 (1991)), 44.8 g (190 mmol) of 1,4-dibromobenzene, 5.6 g (100 mmol) of potassium hydroxide, 1.6 g (25 mmol) of copper powder, and 50 ml of decalin was heated at an external temperature of 200° C. for 36 hours in a nitrogen stream while stirring. The reaction mixture was cooled nearly to room temperature, chloroform was added thereto, followed by filtration using Celite to remove the insoluble matter. The filtrate was concentrated. To remove decalin, n-hexane was added to the residue, followed by filtration. The filter cake was purified by silica gel column chromatography to give 3.8 g (25%) of 9-(4-bromophenyl)-9H-tribenz[b,d,f]azepine.

The resulting azepine (3.0 g; 7.5 mmol) was dissolved in 20 ml of tetrahydrofuran, hereinafter THF, and 41 mg (0.075 mmol) of (1,3-bisdiphenylphosphinopropane) dichloronickel was added to the solution. The mixture was stirred at 0° C. in a nitrogen stream, and 9.0 ml (9.0 mmol) of a 0.1M THF solution of vinylmagnesium bromide was added thereto by means of a syringe. After about 2 hours' stirring, water was added to the reaction mixture, and the mixture was extracted with chloroform. The extract was concentrated and purified by silica gel column chromatography to give 1.9 g (74%) of a vinyl monomer.

The resulting vinyl monomer (10 g) was dissolved in 70 ml of toluene, and 0.3 g of azobisisobutyronitrile (AIBN) was added thereto while stirring at 75° C. in a nitrogen atmosphere. After the mixture was further stirred for 2 hours, another 0.3 g portion of AIBN was added to the mixture, followed by stirring for 4 hours. After cooling to room temperature, methanol was added to the reaction mixture for reprecipitation. The precipitate thus formed was collected by filtration, washed with methanol, and dried to yield 7.8 g of polymer 16. The Mw of polymer 16 was found to be 40200 (on polystyrene conversion) as measured by gel-permeation chromatography.

The luminescent element material comprising polymer A can be used in any of a hole-injecting layer, a hole-transporting layer, an electron-injecting layer, an electron-transporting layer, and a luminescent layer. It is preferred for the luminescent element material to be used in a hole-injecting layer, a hole-transporting layer and a luminescent layer. It is still preferred for the luminescent element material to be used in a hole-injecting layer and a hole-transporting layer.

We will explain the ethylene derivative having a nitrogen-containing 7-membered ring structure represented by formula (IA) below.

The ethylene derivative having a nitrogen-containing 7-membered ring achieves the above objects of the invention, exhibiting high charge transporting ability and storage stability.

As will be understood from the following description, in formula (IA), every group represented by (A), $Ar_1$, $Ar_2$, $R_1$, $R_2$, $R_3$, $R_4$, and $R_5$ includes not only an unsubstituted one but a substituted one.

In formula (IA), (A) represents an ethylene group, a vinylene group or an o-arylene group. Specific examples of (A) as unsubstituted, are as follows:

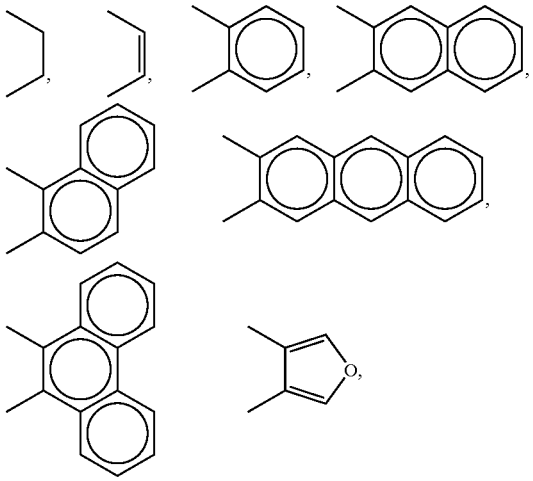

Preferred substituents which may be on (A) in formula (IA) include the groups represented by $R_4$ and $R_5$ hereinafter described. (A) preferably represents a substituted or unsubstituted vinylene group or a substituted or unsubstituted o-phenylene group. An alkyl-substituted or unsubstituted o-phenylene group is still preferred.

$Ar_1$ and $Ar_2$, in formula (IA), each represent a substituted or unsubstituted aryl group and, more specifically, a substituted or unsubstituted phenyl, naphthyl, phenthrenyl or pyrenyl group. Preferred substituents which may be on $Ar_1$ or $Ar_2$ include the groups represented by $R_4$ and $R_5$ hereinafter described. $Ar_1$ and $Ar_2$ each preferably represent a substituted or unsubstituted phenyl group, particularly an unsubstituted or alkyl-substituted phenyl group.

$R_1$ and $R_2$, in formula (IA), each represent a substituted or unsubstituted alkyl or aryl group. It is preferred that they individually represent a straight-chain or branched alkyl group having 1 to 20 carbon atoms or an aryl group having 6 to 36 carbon atoms, particularly an alkyl group having 1 to 6 carbon atoms or an aryl group having 6 to 12 carbon atoms.

Examples of $R_1$ and $R_2$ in formula (IA), as unsubstituted, include methyl, ethyl, isopropyl, n-butyl, t-butyl, n-dodecyl, cyclopentyl, cyclohexyl, phenyl, naphthyl, anthracenyl, phenanthrenyl, pyrenyl, naphthacenyl, pentacenyl, and pentaphenyl groups. Preferred substituents which may be on $R_1$ or $R_2$ include the groups represented by $R_4$ and $R_5$ hereinafter described.

$R_3$ in formula (IA) represents a substituted or unsubstituted alkyl or aryl group. More specifically, $R_3$ has the same meaning as $R_1$ and $R_2$. $R_3$ preferably represents a substituted or unsubstituted alkyl group having 1 to 12 carbon atoms or a substituted or unsubstituted aryl group having 6 to 12 carbon atoms.

$R_4$ and $R_5$ in formula (IA) each represent a halogen atom, a substituted or unsubstituted alkyl group, a substituted or unsubstituted alkenyl group, a substituted or unsubstituted aryl group, a substituted or unsubstituted alkoxy group, a substituted or unsubstituted aryloxy group, a substituted or unsubstituted dialkylamino group, a substituted or unsubstituted N-alkyl-N-arylamino group or a substituted or unsubstituted diarylamino group. The halogen atom and the groups, as unsubstituted, include fluorine, chlorine, bromine, iodine, an alkyl group having 1 to 20 carbon atoms, an alkenyl group having 2 to 20 carbon atoms, an aryl group having 6 to 36 carbon atoms, an alkoxy group having 1 to 20 carbon atoms, an aryloxy group having 6 to 36 carbon atoms, a dialkylamino group having 2 to 20 carbon atoms, an N-alkyl-N-arylamino group having 7 to 42 carbon atoms, and a diarylamino group having 12 to 48 carbon atoms.

Specific examples of $R_4$ and $R_5$ in formula (IA), except for halogen, aremethyl, ethyl, isopropyl, n-butyl, t-butyl, n-dodecyl, and cyclohexyl as for the alkyl group; vinyl, 2-phenyl-1-propen-1-yl, and 2,2-diphenylethenyl as for the alkenyl group; phenyl, naphthyl, anthracenyl, phenanthrenyl, pyrenyl, naphthacenyl, pentacenyl, and pentaphenyl as to the aryl group; methoxy, ethoxy, isopropoxy, n-hexyloxy, cyclohexyloxy, octyloxy, and dodecyloxy as for the alkoxy group; phenoxy, naphthoxy, anthracenoxy, and pentacenoxy as for the aryloxy group; dimethylamino, diethylamino, dibutylamino, dioctylamino and N-ethyl-N-butylamino as for the dialkylamino group; N-methyl-N-phenylamino, N-ethyl-N-phenylamino, N-isopropyl-N-(3-methylphenyl)amino, N-methyl-N-(1-naphthyl)amino, and N-butyl-N-(1-naphthacenyl)amino as for the N-alkyl-N-arylamino group; and diphenylamino, N-phenyl-N-(1-naphthyl)amino, N-(1-naphthyl)-N-(1-naphthyl)amino, N-phenyl-N-(1-anthracenyl)amino and N-(1-anthracenyl)-N-(1-phenanthrenyl) amino as to the diarylamino group.

The substituents which may be on these groups include a halogen atom, an alkyl group, an aryl group, a heterocyclic group, a cyano group, a hydroxyl group, a nitro group, a carboxyl group, a sulfo group, an amino group, an alkoxy group, an aryloxy group, an acylamino group, an alkylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonylamino group, an imido group, a heterocyclic thio group, a sulfinyl group, a phosphonyl group, an aryloxycarbonyl group, an acyl group, a silyl group, and an azolyl group.

It is preferred that $R_4$ and $R_5$ in formula (IA) each represent a halogen atom, an alkyl group, an alkoxy group, a dialkylamino group or a diarylamino group. An alkyl group or a dialkylamino group is particularly preferred as $R_4$ or $R_5$.

$Ar_1$ and $R_1$, or $Ar_2$ and $R_2$, in formula (IA), may be taken together either directly or indirectly to form a ring, preferably a 5- to 7-membered ring.

The positions of $Ar_1(R_1)C=CH-(CH=CH)_m-$ and $Ar_2(R_2)C=CH-(CH=CH)_n-$ on the respective benzene rings are the 2- or 3-position, preferably 2-position, and the 7- or 8-position, preferably 8-position, respectively.

m and n, in formula (IA), each represent an integer of 0 to 2, and p and q each represent an integer of 0 to 3. It is preferred that m and n each represent 0 or 1, particularly 0, and that p and q each represent 0 or 1, particularly 0.

Specific examples of the compound represented by formula (IA) are shown below for illustrative purposes only but not for limitation.

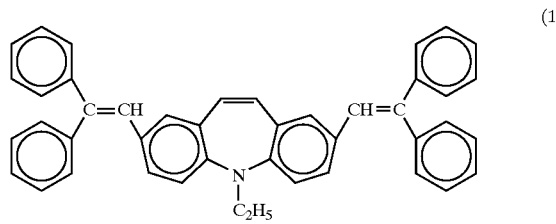

(1A)

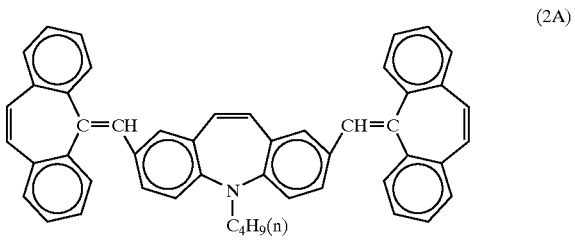

(2A)

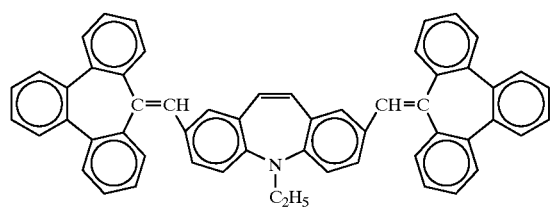

(3A)

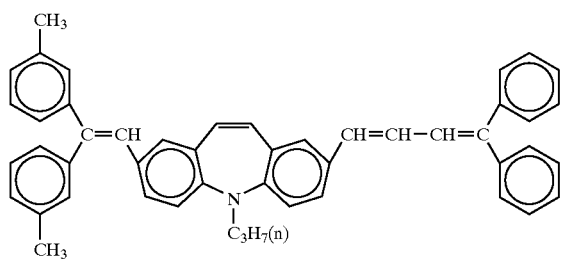
(4A)
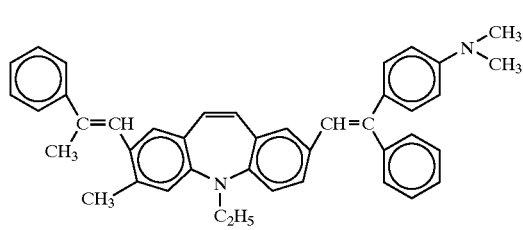
(5A)
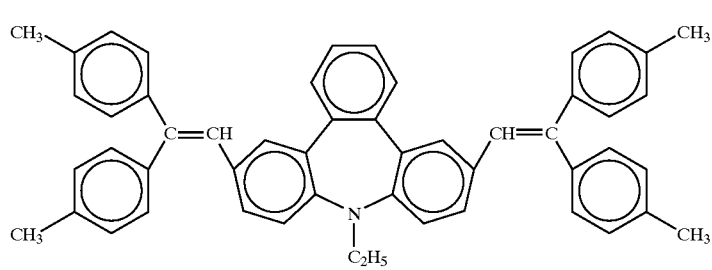
(7A)
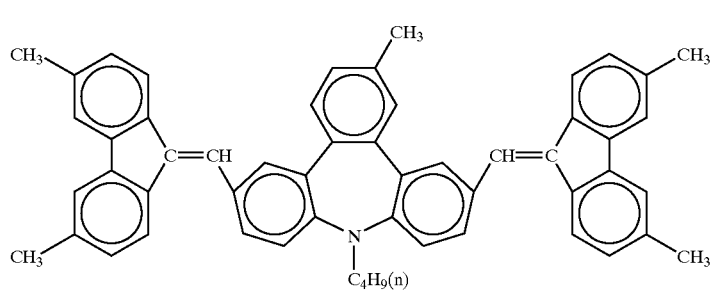
(8A)
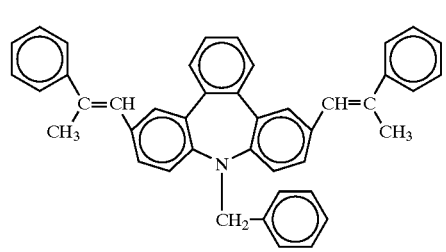
(9A)
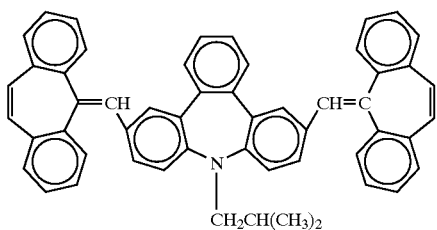
(10A)
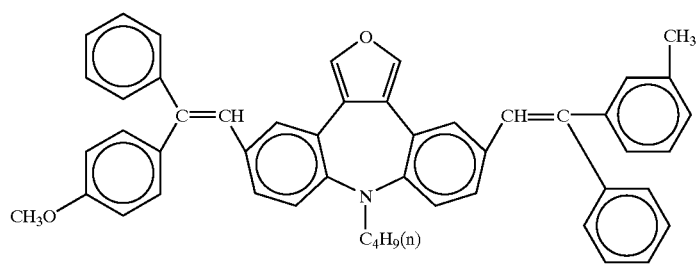
(11A)

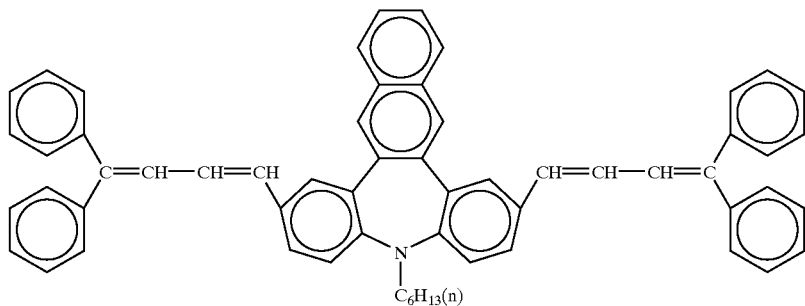
(12A)
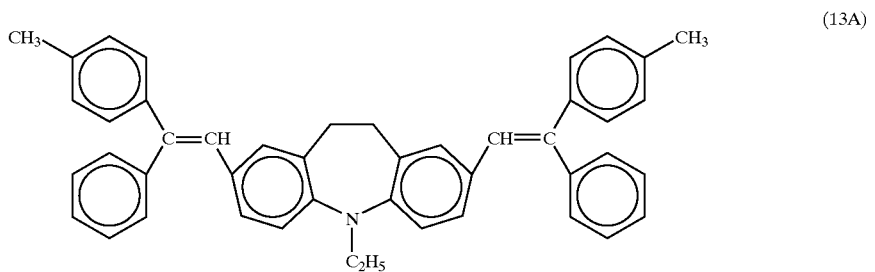
(13A)
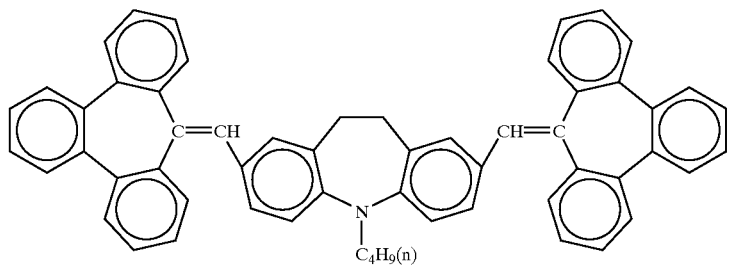
(14A)
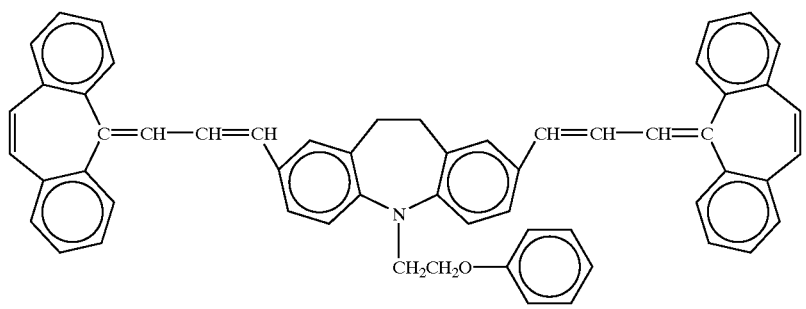
(15A)
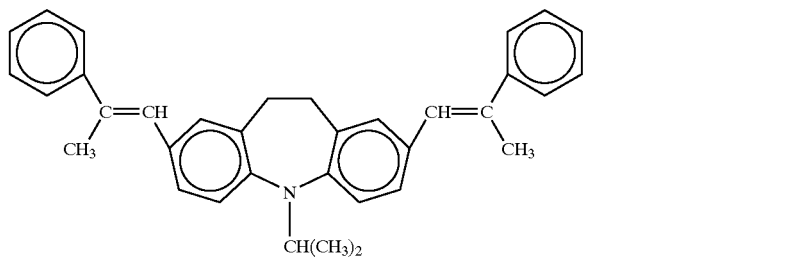
(16A)

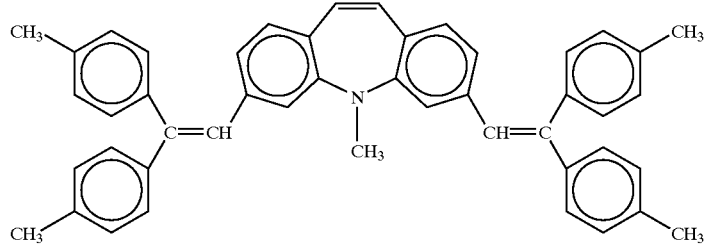
(17A)
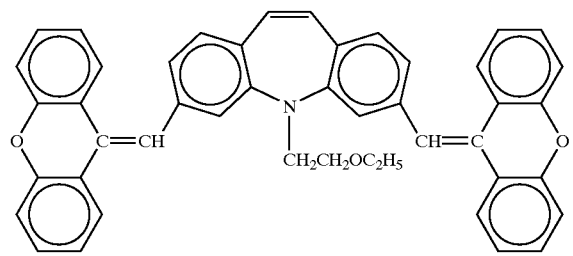
(18A)
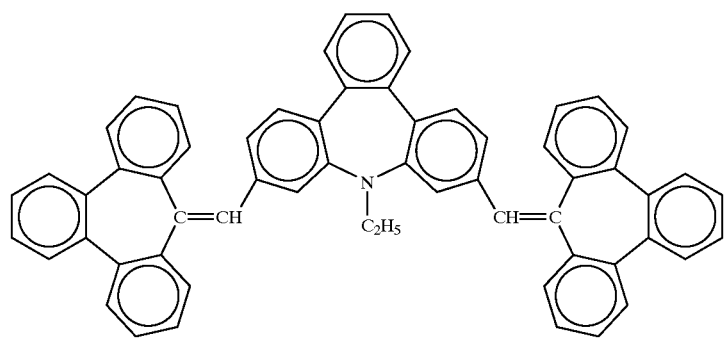
(19A)
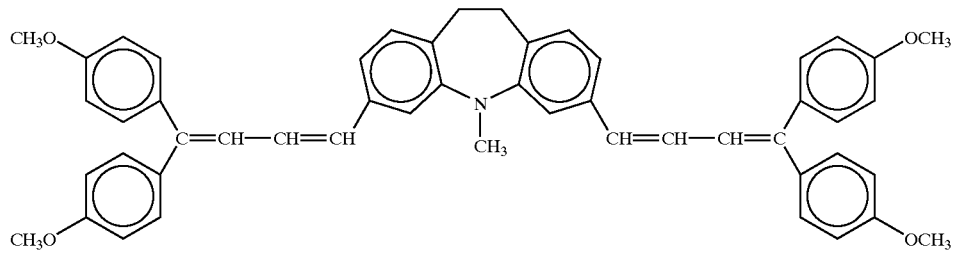
(20A)
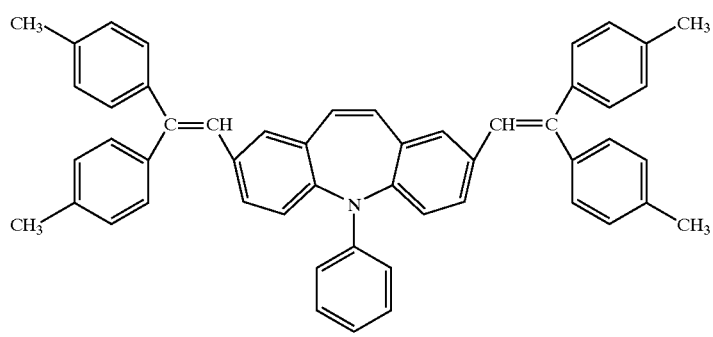
(21A)

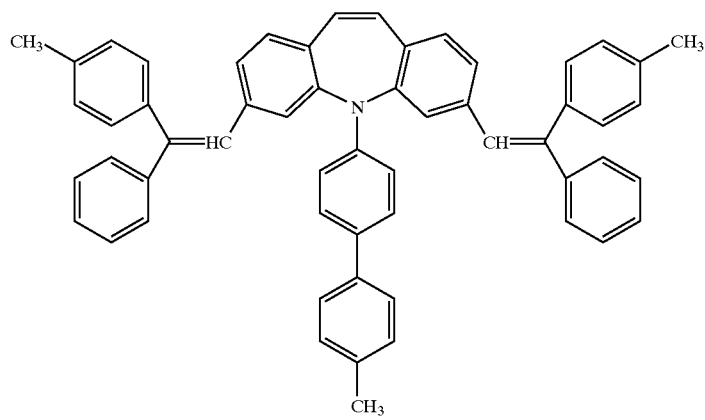
(22A)
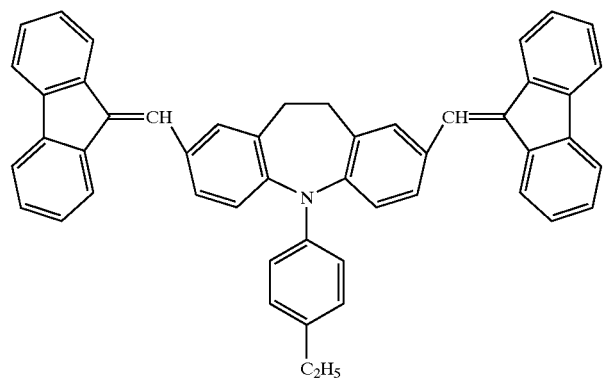
(23A)
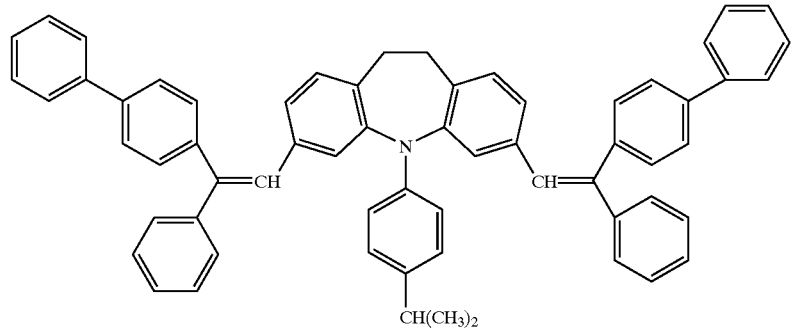
(24A)
The compounds of formula (IA) of the invention can be synthesized typically through the following reaction scheme.
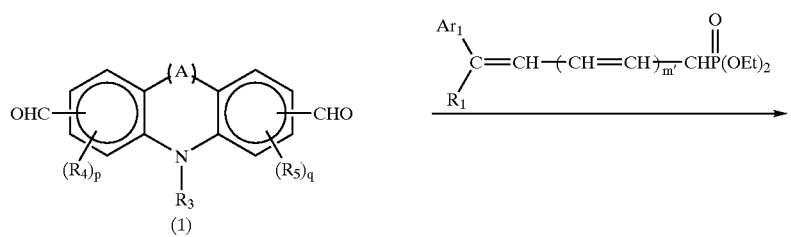

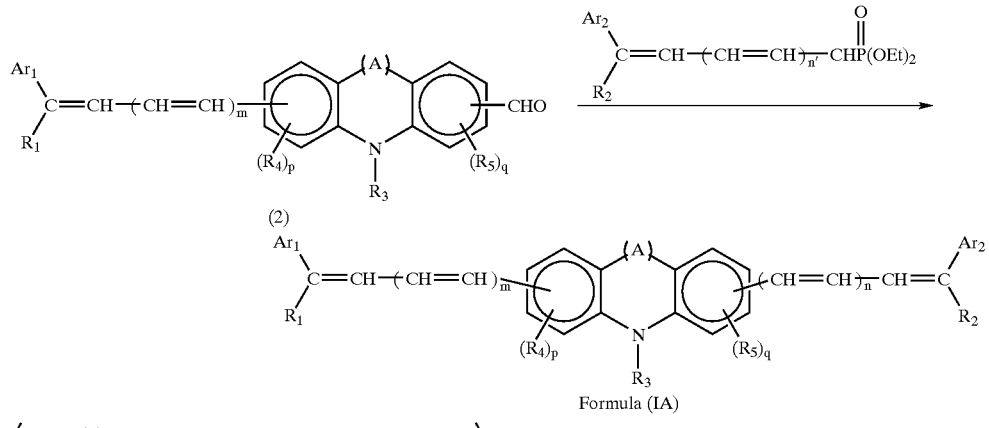

Formula (IA)

(wherein (A), Ar₁, Ar₂, R₁, R₂, R₃, R₄, R₅, m, n, p, and q are as defined above; m' represents an integer satisfying m' + 1 = m (m ≠ 0); and n' represents an integer satisfying n' + 1 = n (n ≠ 0).)

In scheme, the reactions from compound [1] to compound [2] and from compound [2] to compound of formula (IA) (reactions for introducing a double bond) are well known in the art as a Wittig-Horner-Emmons reaction. The reactions are usually carried out in a solvent, such as ethanol, toluene, tetrahydrofuran, dimethylformamide or dimethyl sulfoxide, in the presence of a base, such as a sodium or potassium alkoxide, sodium hydride or sodium amide. For the details, refer to *Shin jikken kagaku koza*, vol. 14-(I),p. 238, Maruzen (1977). It is preferred, while not limiting, that the reactions between the aldehyde compounds [1] or [2] and the phosphonic ester compound are conducted at a molar ratio of 1:0.5 to 1:1.5 at −10° to 100° C. for 0.5 to 48 hours.

The starting compound [1] is synthesized by referring to the process described in B. Renfroe, C. Harrington, G. R. Proctor, *The Chemistry of Heterocyclic Compounds*, vol. 43, part 1, John Wiley & Sons, Inc. (1984).

We will explain the benzoazepine derivative having an ethenyl group represented by formula (IB) below.

In formula (IB), the groups represented by (A), $R_1$, $R_2$, $R_3$, $Y_1$, $Y_2$, and $Y_3$ include not only unsubstituted ones but substituted ones, if possible, as will be understood from the following description.

(A) in formula (IB) represents a substituted or unsubstituted vinylene group or a substituted or unsubstituted arylene group. Substituents that may be on (A) include those which will be described as being represented by $R_1$, $R_2$, and $R_3$. Specific examples of the vinylene and the arylene groups as unsubstituted are shown below. Preferred of them are a substituted or unsubstituted vinylene group and a substituted or unsubstituted o-phenylene group.

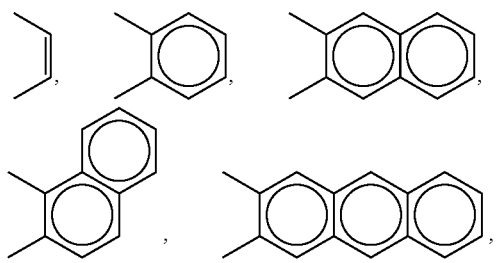

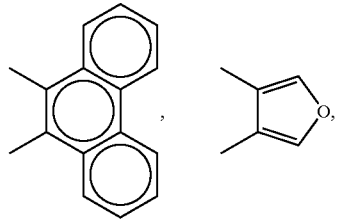

$R_1$, $R_2$, $R_3$, in formula (IB), each represent a hydrogen atom or a substituent. The substituent includes a halogen atom, an alkyl group, an alkenyl group, an aryl group, a heterocyclic group, a cyano group, a hydroxyl group, a nitro group, a carboxyl group, a sulfo group, an amino group, an alkoxy group, an aryloxy group, an acylamino group, a mono- or dialkylamino group, an N-(unsubstituted, alkyl- or aryl-substituted)arylamino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonylamino group, an imido group, a heterocyclic thio group, a sulfinyl group, a phosphonyl group, an aryloxycarbonyl group, an acyl group, a silyl group and an azolyl group. The compound of formula (IB) can have a plurality of $R_1$'s, a plurality of $R_2$'s, and a plurality $R_3$'s on the respective benzene rings. In these cases, the two or more $R_1$'s, $R_2$'s or $R_3$'s may be the same or different.

It is preferred that $R_1$, $R_2$ and $R_3$, in formula (IB), each preferably represent a hydrogen atom, a halogen atom, an alkyl group, an aryl group, an alkoxy group, an aryloxy group, a dialkylamino group, an N-alkyl-N-arylamino group, or a diarylamino group. The halogen atom includes fluorine, chlorine, and bromine. The alkyl group includes substituted or unsubstituted and straight-chain or branched alkyl groups having 1 to 12 carbon atoms, such as methyl, ethyl, n-propyl, n-octyl, n-dodecyl, 2-methoxyethyl, 2-phenylmethyl, benzyl, isopropyl, isobutyl, sec-butyl, t-butyl, t-amyl, t-octyl, cyclopentyl, cyclohexyl, and cycloheptyl groups.

In formula (IB), the aryl group includes substituted or unsubstituted aryl groups having 6 to 20 carbon atoms, such as phenyl, 2-, 3- or 4-methylphenyl, 4-t-butylphenyl, 4-methoxyphenyl, 4-dimethylaminophenyl, 1- or 2-naphthyl, anthryl, and phenanthryl groups. The alkoxy group includes substituted or unsubstituted alkoxy groups having 1 to 6 carbon atoms, such as methoxy, ethoxy, n-propoxy, n-butoxy, n-hexyloxy, isopropoxy, isobutoxy, t-butoxy, cyclopentyloxy, and cyclohexyloxy groups.

In formula (IB), the aryloxy group includes substituted or unsubstituted aryloxy groups having 6 to 20 carbon atoms, such as phenoxy, 2-, 3- or 4-methylphenoxy, 4-t-butylphenoxy, 4-phenylphenoxy, 4-methoxyphenoxy, 2-cyclohexylphenoxy, 3-ethylphenoxy, 1- or 2-naphthoxy, anthryloxy, and phenanthryloxy groups. The dialkylamino group includes substituted or unsubstituted dialkylamino groups having 2 to 16 carbon atoms, such as dimethylamino, diethylamino, dibutylamino, dioctylamino, N-methylbutylamino, bis(2-methoxyethyl)amino, and bis(2-chloroethyl)amino groups.

In formula (IB), the N-alkyl-N-arylamino group includes substituted or unsubstituted N-alkyl-N-arylamino groups having 7 to 21 carbon atoms, such as N-methylanilino, N-butylanilino, and N-methyl-1-naphthylamino groups. The diarylamino group includes substituted or unsubstituted diarylamino groups having 12 to 36 carbon atoms, such as diphenylamino, N-(3-methylphenyl)anilino, N-(4-methylphenyl)anilino, bis(4-methylphenyl)amino, N-naphthylanilino, and dinaphthylamino groups.

It is particularly preferred that $R_1$, $R_2$, and $R_3$, in formula (IB), be each a hydrogen atom or an alkyl group.

$Y_1$, $Y_2$, and $Y_3$, in formula (IB), have the same meaning as $R_1$, $R_2$, and $R_3$, with proviso that at least one of them is an ethenyl group. Specifically, at least one of them is an alkyl-substituted or unsubstituted ethenyl group, preferably a vinyl group or an isopropenyl group, particularly preferably a vinyl group. $Y_1$, $Y_2$, and $Y_3$ are preferably at the para-position with respect to the nitrogen atom.

In formula (IB), n represents an integer of from 0 to 4, preferably an integer of 0 to 2, particularly preferably 1. Where n is 0, $Y_3$ is an alkyl group, an aryl group or an ethenyl group.

Specific but non-limiting examples of the compounds represented by formula (IB) are shown below.

(1B)
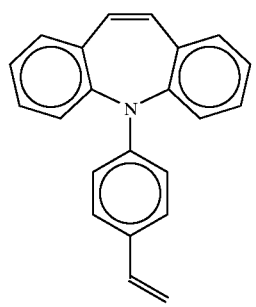

(2B)
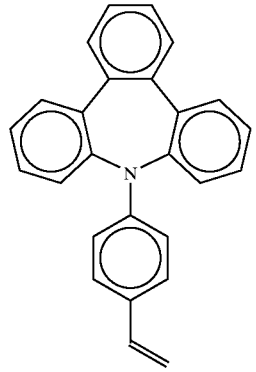

(3B)
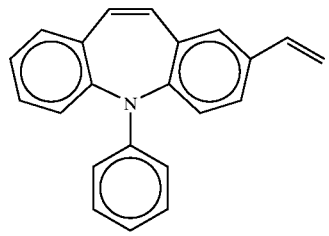

(4B)
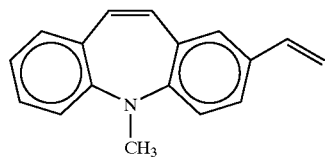

(5B)
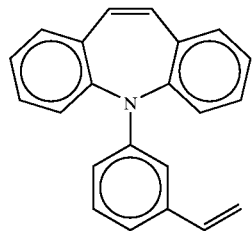

(6B)
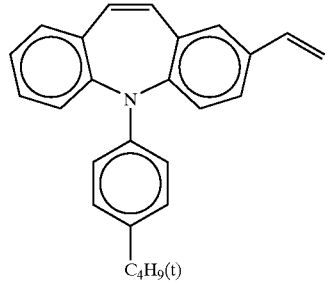

-continued (7B)
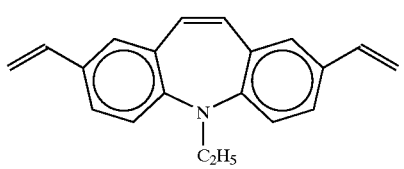

(8B)
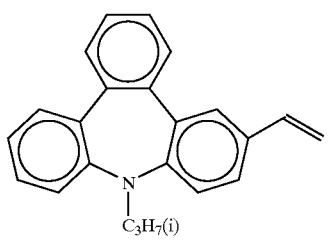

(9B)
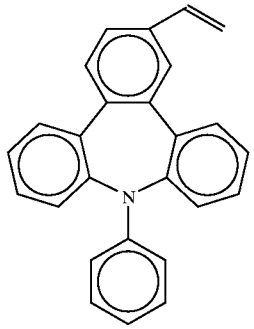

(10B)
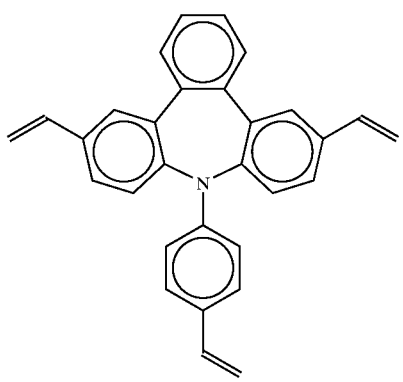

(11B)
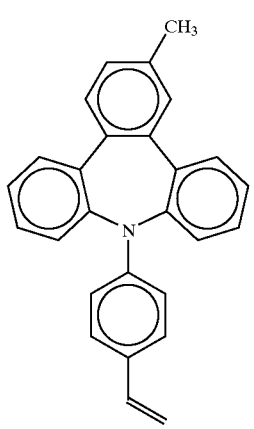

-continued (12B)
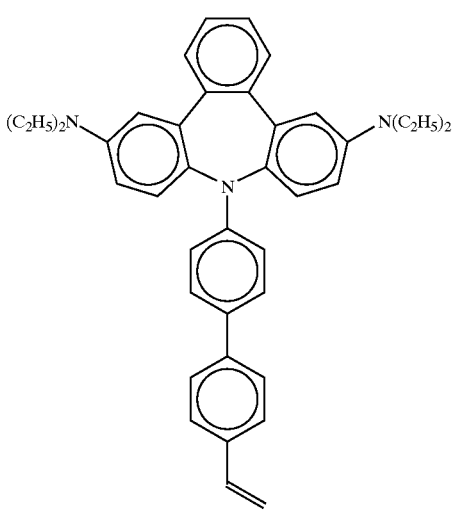

(13B)
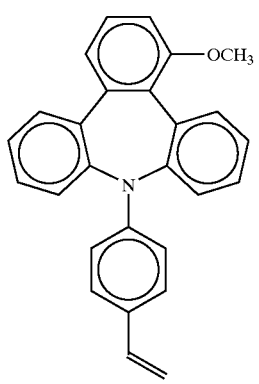

(14B)
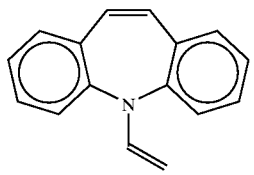

(15B)
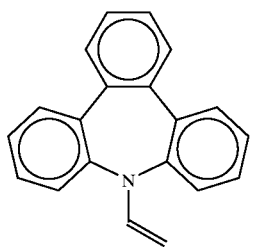

Typical process for preparing the compounds of formula (IB) are shown in the following reaction schemes. The starting benzoazepine compound is synthesized by referring to the process described in B. Renfroe, C. Harrington, G. R. Proctor, *The Chemistry of Heterocyclic Compounds*, vol. 43, part 1, John Wiley & Sons, Inc. (1984) and H. C. Axtell et al., *J. Org. Chem.*, vol. 56, p. 3906 (1991).

(1) $Y_3$ = ethenyl; n ≠ 0
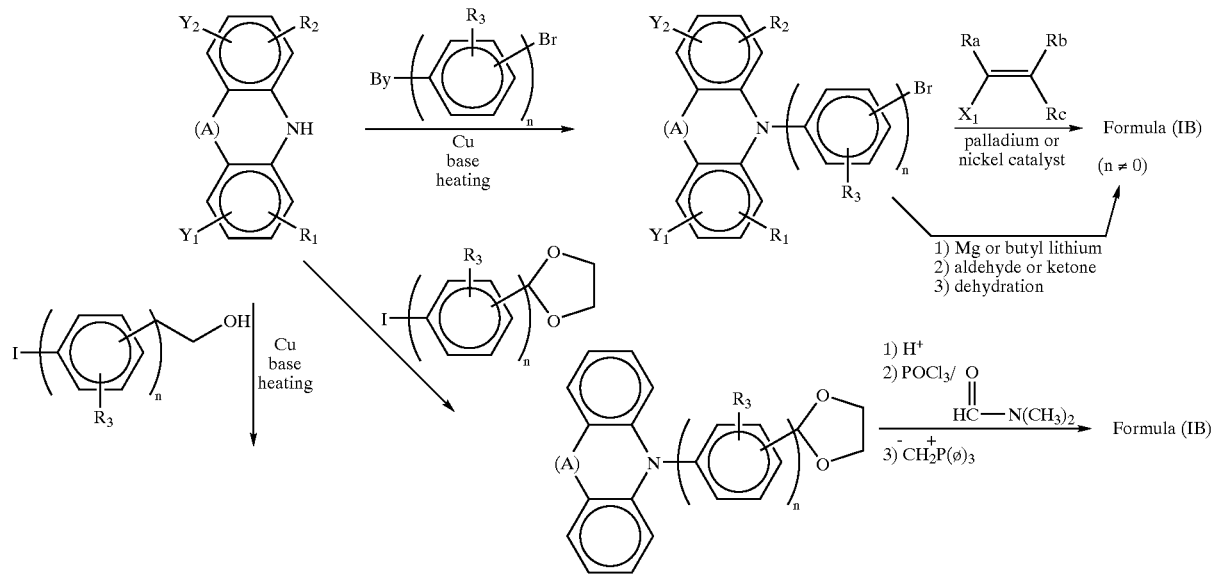
(2) $Y_3$ = ethenyl; n = 0
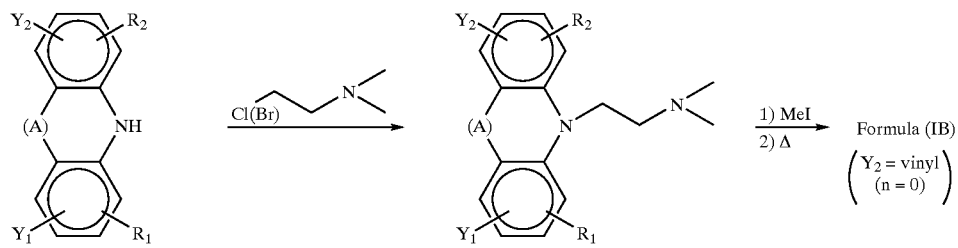

(3) $Y_1$ (or $Y_2$) = ethenyl

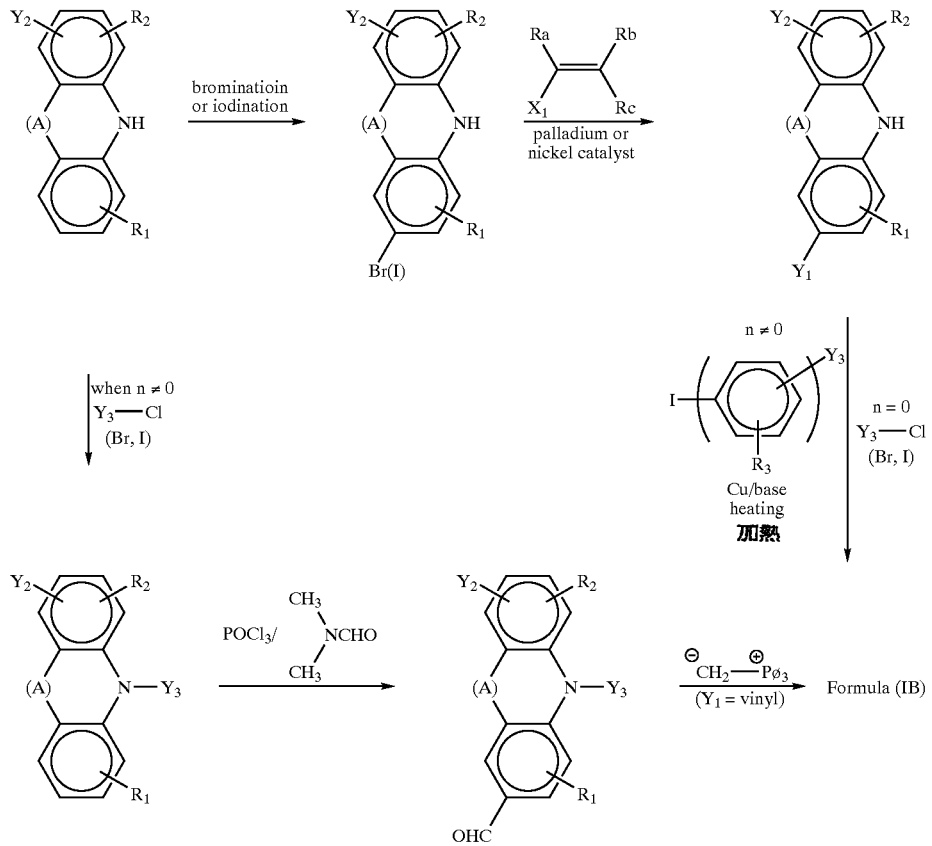

wherein $Y_1$, $Y_3$, $R_1$, $R_2$, $R_3$, Ra, Rb, Rc, $X_1$, and n are as defined above.

The compound of formula (IB) thus prepared can be purified by column chromatography on silica gel and recrystallization. If necessary, sublimation can be conducted.

The luminescent element according to the invention comprises a pair of electrodes (i.e., a positive electrode and a negative electrode) having therebetween a luminescent layer or a plurality of organic compound thin layers containing a luminescent layer. In addition to the luminescent layer, the luminescent element can have organic compound thin layers, such as a hole-injecting layer, a hole-transporting layer, an electron-injecting layer, and an electron-transporting layer, a protective layer, and so forth. Each layer can have other functions in addition to the designated one. At least one of the organic compound thin layers contains the luminescent element material according to the invention. The luminescent element materials of the invention can be used either individually or as a combination of two or more thereof.

The positive electrode is to supply positive holes to the hole-injecting layer, the hole-transporting layer, the luminescent layer, etc. Metals, alloys, metal oxides, electrically conductive compounds, and mixtures thereof can be used as the positive electrode. Materials having a work function of 4 eV or more are preferred.

Examples of useful materials for the positive electrode include conductive metal oxides, such as tin oxide, zinc oxide, indium oxide, and indium-tin oxide (ITO); metals, such as gold, silver, chromium, and nickel; mixtures or laminae of the metal and the conductive metal oxide; inorganic conductive substances, such as copper iodide and copper sulfide; organic conductive materials, such as polyaniline, polythiophene, and polypyrrole; and laminates of these materials and ITO. Conductive metal oxides are preferred. ITO is particularly preferred for productivity, high conductivity, and transparency.

The thickness of the positive electrode is selected appropriately according to the material. It is usually 10 nm to 5 $\mu$m, preferably 50 nm to 1 $\mu$m, still preferably 100 nm to 500 nm.

The positive electrode is usually formed in a layer on a substrate, such as a soda-lime glass plate, an alkali-free glass plate or a transparent plastic plate. Of the glass materials, alkali-free glass is preferred so as to minimize ions dissolving from glass. In using soda-lime glass, it is desirable to provide a barrier coat, such as silica. The substrate may be as thin as is consistent with mechanical strength, but it is usually desirable for a glass substrate to be at least 0.2 mm thick, particularly at least 0.7 mm thick.

The positive electrode can be formed by various methods according to the material. For example, an ITO film electrode can be formed by electron beam deposition, sputtering deposition, resistance heating vacuum-evaporation, sol-gel process, coating with an ITO dispersion, and the like.

The positive electrode can be subjected to a treatment, such as washing, so as to reduce the driving voltage of the element or to increase luminescence efficiency. For example, a UV-ozone treatment of an ITO electrode is effective.

The negative electrode is to supply electrons to the electron-injecting layer, the electron-transporting layer, the luminescent layer, etc. The negative electrode material is selected from metals, alloys, metal oxides, electrically conductive compounds, and mixtures thereof, taking into consideration adhesion to the adjacent layer, such as the electron-injecting layer, the charge-transporting layer or the luminescent layer, ionizing potential, stability, and the like. Examples of useful materials include alkali metals (e.g., Li, Na, and K) or fluorides thereof, alkaline earth metals (e.g., Mg and Ca) or fluorides thereof; gold, silver, lead, aluminum; a sodium-potassium alloy or mixture thereof; a lithium-aluminum alloy or mixture; a magnesium-silver alloy or mixture; and rare earth metals, such as indium and yttrium. Materials having a work function of 4 eV or more are preferred. Aluminum, a lithium-aluminum alloy or mixture, and a magnesium-silver alloy or mixture are still preferred.

The thickness of the negative electrode is selected appropriately according to the material. It is usually 10 nm to 5 $\mu$m, preferably 50 nm to 1⁻ $\mu$m, still preferably 100 nm to 500 nm.

The positive electrode is formed by electron beam deposition, sputtering deposition, resistance heating vacuum evaporation, coating, and the like. A single metal may be deposited, or two or more metals may be deposited simultaneously. A plurality of metals may be deposited simultaneously to form an alloy electrode. A previously prepared alloy may be deposited. The sheet resistivity of the positive and negative electrodes is preferably as low as possible, e.g., several hundreds of ohms or less per square.

The luminescent layer can be made of any of materials into which holes can be injected from the positive electrode, the hole-injecting layer or the hole-transporting layer and, at the same time, into which electrons can be injected from the negative electrode, the electron-injecting layer or the electron-transporting layer on voltage application, materials through which the injected charges can be migrated, and materials which provide the site where holes and electrons are recombined to generate light output. The luminescent layer can also comprise luminescent element materials other than the luminescent element material of the invention.

Useful luminescent element materials other than the luminescent element material of the invention include various metal complexes typically exemplified by metal complex or rare earth complex of benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, styrylamine derivatives, aromatic dimethylidyne compounds, and 8-quinolinol derivatives; and polymeric compounds, such as polythiophene, polyphenylene, and polyphenylenevinylene.

While not limiting, the luminescent layer usually has a thickness of 1 nm to 5 $\mu$m, preferably 5 nm to 1 $\mu$m, still preferably 10 nm to 500 nm.

The luminescent layer can be formed by, for example, resistance heating vacuum evaporation, electron beam deposition, sputtering deposition, molecular lamination, coating (spin coating, casting, dip coating, etc.), a Langmuir-Blodgett, hereinafter "LB", method, and so forth. Resistance heating vacuum evaporation or coating is preferred.

The hole-injecting layer and the hole-transporting layer can be of materials that have any one of a function of injecting holes from the positive electrode, a function of transporting the holes, and a function of blocking the electrons injected from the negative electrode. Examples of such materials include not only the Luminescent element material according to the invention but carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrinic compounds, polysilane compounds, poly(N-vinylcarbazole) derivatives, aniline copolymers, conductive oligomers, such as thiophene oligomers, polythiophene, and the like.

While not limiting, the thickness of the hole-injecting layer or the hole-transporting layer is usually 1 nm to 5 $\mu$m, preferably 5 nm to 1 $\mu$m, still preferably 10 nm to 500 nm. The hole-injecting layer and the hole-transporting layer may have a single layer structure made up of one or more than one of the above-described materials, or a multilayer structure in which a plurality of layers have the same composition or different compositions.

The hole-injecting layer and the hole-transporting layer can be formed by, for example, vacuum evaporation, an LB method, or coating (spin coating, casting, dip coating, etc.) with a solution or dispersion of a hole-injecting and/or transporting compound in a solvent. The solution or dispersion used for coating can contain a resin component, such as polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethyl cellulose, polyvinyl acetate, ABS resins, polyurethane, melamine resins, unsaturated polyester resins, alkyd resins, epoxy resins, and silicone resins.

The electron-injecting layer and the electron-transporting layer can be made of a material that has any one of a function of injecting electrons from the negative electrode, a function of transporting electrons, and a function of blocking the holes injected from the positive electrode. Examples of such a material include not only the Luminescent element material of the invention but various metal complexes typically exemplified by metal complexes of triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, tetracarboxylic acid of a condensed ring such as naphthalene and perylene, phthalocyanine derivatives, and 8-quinolinol derivatives; metal phthalocyanine; and metal complexes containing benzoxazole or benzothiazole as a ligand.

While not limiting, the thickness of the electron-injecting layer and the electron-transporting layer is usually 1 nm to 5 $\mu$m, preferably 5 nm to 1 $\mu$m, still preferably 10 nm to 500 nm. The electron-injecting layer and the electron-transporting layer may have a single layer structure made up of one or more than one of the above-described materials, or a multilayer structure in which a plurality of layers have the same composition or different compositions.

The electron-injecting layer and the electron-transporting layer can be formed by, for example, vacuum evaporation, an LB method, or coating (spin coating, casting, dip coating, etc.) with a solution or dispersion of a electron-injecting and/or transporting compound in a solvent. The solution or dispersion used for coating can. contain such a resin component as mentioned above with respect to the hole-injecting layer and the hole-transporting layer.

The protective layer can be made of any material that prevents substances which may accelerate deterioration of a luminescent element, such as moisture and oxygen, from entering the element. Such materials include metals, e.g., In, Sn, Pb, Au, Cu, Ag, Al, Ti, and Ni; metal oxides, e.g., MgO, SiO, $SiO_2$, $Al_2O_3$, GeO, NiO, CaO, BaO, $Fe_2O_3$, $Y_2O_3$, and $TiO_2$; metal fluorides, e.g., $MgF_2$, LiF, $AlF_3$, and $CaF_2$; polyethylene, polypropylene, polymethyl methacrylate, polyimide, polyurea, polytetrafluoroethylene, polychlorotrifluoroethylene, polydichlorodifluoroethylene, chlorotrifluoroethylene-dichlorodifluoroethylene copolymers, tetrafluoroethylene copolymers, fluorine-containing copolymers having a cyclic structure in the main chain thereof, water absorbing materials having a water absorption of 1% or more, and moistureproof materials having a water absorption of 0.1% or less.

The protective layer can be formed by, for example, vacuum evaporation, sputtering deposition, reactive sputtering deposition, molecular beam epitaxy, ionized cluster beam deposition, ion plating, plasma polymerization (RF-excited ion plating), plasma-enhanced CVD, laser-assisted CVD, thermal CVD, gas source CVD, coating, and the like.

The present invention will now be illustrated in greater detail by way of Examples, but it should be understood that the invention is not limited thereto.

EXAMPLE 1

A cleaned ITO substrate was spin coated with a solution of 40 mg of the compound shown in Table 1 in 3 ml of 1,2-dichloroethane to a thickness of about 40 nm. Tris(8-hydroxyquinolinato)aluminum (Alq) was deposited thereon by vacuum evaporation ($8 \times 10^{-6}$ to $1 \times 10^{-5}$ Torr) to a deposit thickness of about 60 nm. A pattern mask which provides a light-emitting area of 5 mm×5 mm was put on the organic thin film, and magnesium:silver=10:1 were co-deposited in a vacuum evaporation system to a thickness of 250 nm, and then silver was vacuum deposited ($8 \times 10^{-6}$ to $1 \times 10^{-5}$ Torr) to a thickness of 300 nm to prepare a luminescent element (designated samples 101 to 113).

Luminescent characteristics of the resulting luminescent elements were evaluated as follows. A constant direct voltage was applied between the ITO positive electrode and the Mg:Ag negative electrode of the luminescent elements by means of Source Measure Unit 2400 (manufactured by Toyo Corp.). The brightness and the wavelength of the emitted light were measured with a brightness meter BM-8 (manufactured by Topcon Co., Ltd.) and a spectrum analyzer PMA-11 (manufactured by Hamamatsu Photonics), respectively. Further, the elements were allowed to stand at 60° C. and 20% RH for 3 hours, and the brightness of emitted light was measured in the same manner. The brightness after aging was expressed in terms of a relative brightness, taking the brightness immediately after the element preparation as 100 (driving voltage: 15 V). The results obtained are shown in Table 1.

TABLE 1

| Sample No. | Compound | Luminescent Wavelength $\lambda_{max}$ (nm) | Maximum Brightness (cd/m$^2$) | Minimum Driving Voltage (V) | Relative Brightness after Aging | Remark |
|---|---|---|---|---|---|---|
| 101 | a* | 515 | 155 | 12 | 42 | comparison |
| 102 | b* | 514 | 328 | 11 | 28 | " |
| 103 | c* | 515 | 302 | 11 | 33 | " |
| 104 | d* | 515 | 347 | 11 | 36 | " |
| 105 | polymer 1 | 516 | 1320 | 8 | 88 | invention |
| 106 | polymer 10 | 520 | 1570 | 8 | 78 | " |
| 107 | polymer 13 | 518 | 2060 | 7 | 86 | " |
| 108 | polymer 16 | 515 | 2720 | 6 | 88 | " |
| 109 | polymer 33 | 517 | 1083 | 8 | 80 | " |
| 110 | polymer 36 | 518 | 1650 | 7 | 85 | " |
| 111 | polymer 42 | 516 | 2120 | 7 | 86 | " |
| 112 | polymer 43 | 515 | 1680 | 8 | 76 | " |
| 113 | polymer 48 | 515 | 1830 | 7 | 80 | " |

*Comparative compounds having the following structures:

Comparative compound a (PVK):

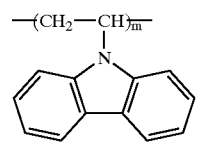

Comparative compound b:

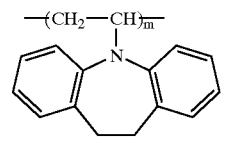

Comparative compound c:

TABLE 1-continued

| Sample No. | Compound | Luminescent Wavelength λ_max (nm) | Maximum Brightness (cd/m²) | Minimum Driving Voltage (V) | Relative Brightness after Aging | Remark |
|---|---|---|---|---|---|---|

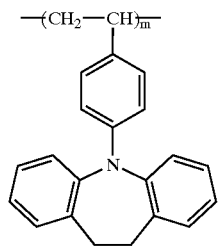

Comparative compound d:

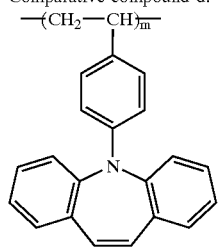

It is seen from Table 1 that the luminescent elements according to the invention (samples 105 to 113) are capable of high brightness electroluminescence at a low minimum driving voltage. These elements were also proved excellent in durability, showing high brightness retention after high temperature storage.

EXAMPLE 2

Luminescent elements (designated samples 201 to 206) were prepared in the same manner as in Example 1, except for using a solution of 37 mg of the compound shown in Table 2 below, 12 mg of compound A (electron-transporting compound) shown below, and 3 mg of compound B (Luminescent element material) shown below in 3 ml of 1,2-dichloroethane. The results of evaluation on luminescent characteristics are shown in Table 2.

Compound A:

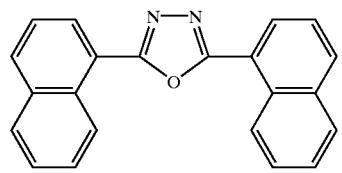

Compound B:

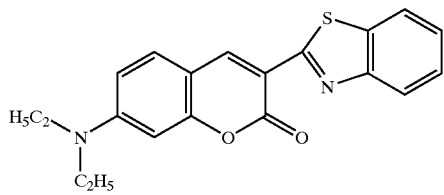

TABLE 2

| Sample No. | Compound | Luminescent Wavelength λ_max (nm) | Maximum Brightness (cd/m²) | Minimum Driving Voltage (V) | Relative Brightness after Aging | Remark |
|---|---|---|---|---|---|---|
| 201 | a* | 523 | 612 | 13 | 30 | comparison |
| 202 | b* | 524 | 425 | 12 | 38 | " |
| 203 | c* | 525 | 505 | 12 | 36 | " |
| 204 | polymer 10 | 524 | 1520 | 8 | 78 | invention |
| 205 | polymer 13 | 523 | 1840 | 9 | 85 | " |
| 206 | polymer 16 | 525 | 2350 | 7 | 88 | " |

The same comparative compounds as used in Example 1.

As is apparent from the results in Table 2, the luminescent elements using the Luminescent element material according to the invention as a host material and, as dopants, a conventional Luminescent element material and an electron-transporting compound (samples 204 to 206) are capable of high brightness electroluminescence at low minimum driving voltages. Also, the luminescent elements of the invention are excellent in durability as understood from the small reduction in brightness after high temperature storage.

EXAMPLE 3

In 3 ml of 1,2-dichloroethane were dissolved 40 mg of the compound shown in Table 3 below, 10.0 mg of a blue light-emitting material B having the following structural formula, 2.0 mg of a green light-emitting material G having the following structural formula, 0.5 mg of a red light-emitting material R1 having the following structural formula, 0.5 mg of a red light-emitting material R2 having the following formula, and 12.0 mg of compound A used in Example 2. A cleaned ITO substrate was spin coated with the solution to form an organic thin film having a thickness of about 110 nm. A patterning mask giving a light-emitting area of 5 mm×5 mm was placed on the organic thin film, and magnesium:silver=10:1 were co-deposited thereon in a vacuum evaporation system to a deposit thickness of 50 nm. Silver was further vacuum deposited to a thickness of 150 nm to obtain a luminescent element (designated samples 301 to 303). The results of evaluation on luminescent characteristics are shown in Table 3.

Green Light-emitting Material G:

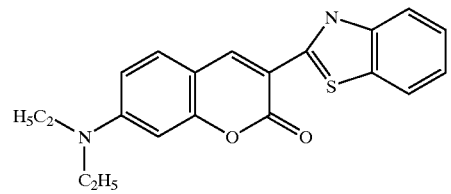

Red Light-emitting Material R1:

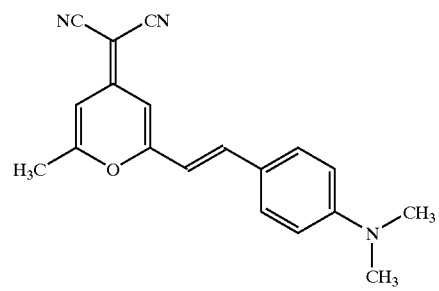

Red Light-emitting Material R2:

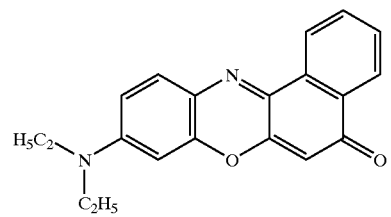

TABLE 3

| Sample No. | Compound | Minimum Driving Voltage (V) | Maximum Brightness (cd/m$^2$) | CEI Chromaticity Coordinates (x, y) | Dark Spot Development ** | Remark |
|---|---|---|---|---|---|---|
| 301 | a* | 14 | 358 | (0.35, 0.36) | observed | comparison |
| 302 | polymer 20 | 9 | 2805 | (0.35, 0.36) | not observed | invention |
| 303 | polymer 31 | 9 | 3922 | (0.34, 0.36) | not observed | " |

*The same comparative compound a as used in Example 1.
** The element was made to emit light after being allowed to stand at 60° C. and 20% RH for 3 hours, and development of dark spots (non-emitting areas) was observed with the naked eye.

Blue Light-emitting Material B:

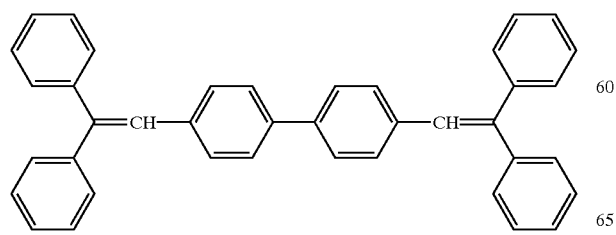

The results in Table 3 demonstrate that the luminescent elements according to the invention (samples 302 to 303) are capable of high brightness electroluminescence at low driving voltages. Compared with the comparative element (sample 301) which suffered from considerable development of dark spots after storage in high temperature, the luminescent elements of the invention retained satisfactory electroluminescence all over the working area. It is also seen that satisfactory white light emission can be obtained by a combined use of the Luminescent element material of the invention with a blue light emitting material, a green light emitting material, and a red light emitting material.

The present invention makes it feasible to achieve high brightness emission at a low driving voltage and to provide a luminescent element with improved durability. In particular, the invention provides a luminescent element exhibiting satisfactory luminescent characteristics even where it is prepared by a coating system, which is highly advantageous for reduction of production cost.

EXAMPLE 4

Synthesis of Compound (1A)

To a solution of 6.4 g (23.0 mmol) of 2,8-diformyl-5-ethyl-5H-benz[d,f]azepine and 15.2 g (50.0 mmol) of diethyl diphenylmethylphosphonate in 70 ml of dimethyl sulfoxide, hereinafter DMSO, was added 6.0 g (50.0 mmol) of 95% potassium t-butoxide, and the mixture was stirred at room temperature for about 10 hours. Water was added to the reaction mixture, and the mixture was extracted with chloroform. The extract was concentrated and purified by column chromatography to give 9.3 g (70%) of compound (1A) as white crystals. Melting point: 173 to 176° C.

EXAMPLE 5

Synthesis of Compound (2A)

In a mixed solvent of methanol and tetrahydrofuran, hereinafter THF, was dissolved 10.0 g (48.5 mmol) of 5H-dibenz[a,d]dichlorohepten-5-one, and 41.0 g (26.4 mmol) of NaBH was added thereto in small portions. After the mixture was stirred for about 2 hours, water was added thereto, followed by extraction with ethyl acetate. The extract was concentrated and recrystallized from methanol to give 9.6 g (95%) of 5-hydroxy-5H-dibenz[a,d]cycloheptene.

The 5-hydroxy-5H-dibenz[a,d]cycloheptene (9.0 g, 43.2 mmol) was mixed with 50 ml of acetyl bromide, followed by heating under reflux for about 30 minutes. The excess acetyl bromide was removed by evaporation under reduced pressure, and 70 g (421 mmol) of triethyl phosphite was added to the residue. The mixture was slowly heated up to 150° C. (external temperature), at which the mixture was kept for about 2.5 hours while driving the by-produced bromoethane out of the system. The excess triethyl phosphite was removed by evaporation under reduced pressure, water added to the residue, and the mixture extracted with ethyl acetate. The extract was purified by silica gel column chromatography to yield 11.3 g (80%) of 5H-dibenz[a,d]cycloheptenyl phosphonate.

In 100 ml of DMSO were dissolved 10.0 g (30.5 mmol) of the 5H-dibenz[a,d]cycloheptenyl phosphonate and 4.2 g (13.9 mmol) of 2,8-diformyl-5-n-butyl-5H-dibenz[d,f]azepine, and 3.6 g (30.5 mmol) of potassium t-butoxide was added to the solution. The mixture was allowed to react and worked up in the same manner as in Example 1 to afford 6.5 g (72%) of compound (2A) as white crystals. Melting point: 180 to 183° C.

EXAMPLE 6

Synthesis of Compound (3A)

In the same manner as in Example 2, 5-hydroxy-5H-tribenz[a,d,f]cycloheptene was synthesized from tribenzocycloheptatrienone, brominated, and sulfonated to synthesize 5H-tribenz[a,d,f]cycloheptenylphosphonate at a content of 75%. The resulting phosphonate was allowed to react with 2,8-diformyl-5-ethyl-5H-dibenz[d,f]azepine in the same manner as in Example 2 to give compound (3A) in a yield of 71%. Melting point: 190 to 192° C.

EXAMPLE 7

Synthesis of Compound (13A)

In the same manner as in Example 1, 2,8-diformyl-10,11-dihydro-5-ethyl-5H-dibenz[d,f]azepine and diethyl 4-methyldiphenylmethylphosphonate were allowed to react to give compound (13A) at a content of 68%. Melting point: 135 to 138° C.

EXAMPLE 8

Synthesis of Compound (14A)

In the same manner as in Example 3, 5H-tribenzo[a,d,f]cycloheptenyl phosphonate was synthesized from tribenzocycloheptatrienone, and the product was allowed to react with 5-butyl-2,8-diformyl-10,11-dihydro-5H-dibenz[d,f]azepine to furnish compound (14A) as white crystals in a yield of 70%. Melting point: 178 to 181° C.

EXAMPLE 9

Synthesis of Compound (21A)

In the same manner as in Example 1, 2,8-diformyl-5-phenyl-5H-dibenz[d,f]azepine and diethyl 4,4'-dimethyldiphenylmethylphosphonate were allowed to react to give compound (21A) in a yield of 65%. Melting point: 125 to 128° C.

The novel ethylene derivative according to the invention has excellent charge transporting ability and storage stability to provide an electrophotographic photoreceptor or an organic EL element with improved performance. In particular, the compound of the invention provides an electrophotographic photoreceptor with highly improved performance.

EXAMPLE 10

Synthesis of Compound (1B)

A mixture of 8.7 g (45 mmol) of 5H-dibenz[b,f]azepine, 12.4 g (50 mmol) of p-iodophenethyl alcohol, 2.8 g (50 mmol) of potassium hydroxide, 4.8 g (75 mmol) of copper powder, and 20 ml of decalin was heated at an external temperature of 200° C. while stirring in a nitrogen stream for 40 hours. The reaction mixture was cooled nearly to room temperature, chloroform was added thereto, followed by filtration using Celite to remove any insoluble matter. The filtrate was concentrated. To remove decalin, n-hexane was added to the residue, followed by filtration. The filter cake was reprecipitated in methanol, and the resulting crude product was purified by silica gel column chromatography to give 4.2 g (30%) of 5-(4-(2-hydroxyethyl)phenyl)-5H-dibenz[b,f]azepine.

The resulting azepine (4.0 g; 12.8 mmol) was dissolved in 20 ml of tetrahydrofuran, hereinafter THF, and 1.8 ml (13.0 mmol) of triethylamine was added to the solution. To the mixture was added 2.5 g (13.0 mmol) of p-toluenesulfonyl chloride, followed by stirring at room temperature for 3 hours. The reaction mixture was extracted with ethyl acetate, and the extract was dried and concentrated. The residue was dissolved in THF, and 1.5 g (13.0 mmol) of 95% potassium t-butoxide was added thereto, followed by gradually heating to a refluxing temperature. About 1 hour's refluxing, the reaction mixture was extracted with chloroform, and the residue was recrystallized from THF/methanol to give 2.8 g (75%) of compound (1B).

NMR Spectrum δ (CDCl$_3$):
5.3 (1H, d, J=10.5), 5.8 (1H, d, J=17.0), 6.2 (2H, d, J=8.0), 6.8 (2H, s), 6.9 (1H, dd, J=10.5, 17.0), 7.0 (2H, d, J=8.0), 76.3–7.5 (8H, m).

EXAMPLE 11

Synthesis of Compound (2B)

A mixture of 9.2 g (38 mmol) of 9H-tribenz[b,d,f]azepine (synthesized in accordance with J. Org. Chem., vol. 56, p. 3906 (1991)), 44.8 g (190 mmol) of 1,4-dibromobenzene, 5.6 g (100 mmol) of potassium hydroxide, 1.6 g (25 mmol) of copper powder, and 50 ml of decalin was heated at an external temperature of 200° C. for 36 hours in a nitrogen stream while stirring. The reaction mixture was worked up in the same manner as in Example 1, and the resulting crude product was purified by silica gel column chromatography to give 3.8 g (25%) of 9-(4-bromophenyl)-9H-tribenz[b,d,f]azepine.

The resulting azepine (3.0 g; 7.5 mmol) was dissolved in 20 ml of THF, and 41 mg (0.075 mmol) of (1,3-bisdiphenylphosphinopropane)dichloronickel was added to the solution. The mixture was stirred at 0° C. in a nitrogen stream, and 9.0 ml (9.0 mmol) of a 0.1M THF solution of vinylmagnesium bromide was added thereto by means of a syringe. After about 2 hours' stirring, water was added to the reaction mixture, and the mixture was extracted with chloroform. The extract was concentrated and purified by silica gel column chromatography to give 1.9 g (74%) of compound (2B).

NMR spectrum δ (CDCl$_3$):
5.5 (1H, d, J=10.2), 5.9 (1H, d, J=17.2), 6.4 (2H, d, J=8.0), 6.9 (1H, dd, J=10.2, 17.2), 7.0 (2H, d, J=8.0), 7.4–7.8 (12H, m).

What is claimed is:

1. A compound represented by formula (IA):

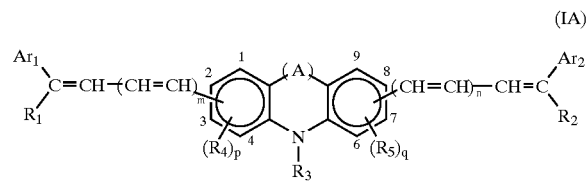

(IA)

wherein (A) represents a vinylene group or an o-arylene group; $Ar_1$ and $Ar_2$ each represent an aryl group; $R_1$ and $R_2$ each represent an alkyl group or an aryl group; $R_3$ represents an alkyl group or an aryl group; $R_4$ and $R_5$ each represent a halogen atom, an alkyl group, an aryl group, an alkoxy group, an aryloxy group, a dialkylamino group, an N-alkyl-N-arylamino group or a diarylamino group; or $Ar_1$ and $R_1$, or $Ar_2$ and $R_2$ are taken together either directly or indirectly to form a ring; $Ar_1(R_1)C=CH-(CH=CH)_m-$ and $Ar_2(R_2)C=CH-(CH=CH)_n-$ are on the 2- or 3-position and the 7- or 8-position of the respective benzene rings; m and n each represent an integer of from 0 to 2; and p and q each represent an integer of from 0 to 3.

2. The compound of claim 1, wherein (A) is a substituted or unsubstituted vinylene group.

3. The compound of claim 1, wherein (A) is a substituted or unsubstituted o-arylene group.

4. The compound of claim 3, wherein (A) is a substituted or unsubstituted o-phenylene group.

5. The compound of claim 4, wherein (A) is an alkyl-substituted o-phenylene group.

6. The compound of claim 1, wherein $Ar_1$ and $Ar_2$ are each selected from the group consisting of substituted or unsubstituted phenyl, substituted or unsubstituted naphthyl, substituted or unsubstituted phenanthrenyl and substituted or unsubstituted pyrenyl groups.

7. The compound of claim 1, wherein $Ar_1$ and $Ar_2$ are independently a substituted or unsubstituted phenyl group.

8. The compound of claim 7, wherein $Ar_1$ and $Ar_2$ are independently an alkyl-substituted or unsubstituted phenyl group.

9. The compound of claim 1, wherein $R_1$ and $R_2$ are independently a straight-chain or branched alkyl group having 1 to 20 carbon atoms or an aryl group having 6 to 36 carbon atoms.

10. The compound of claim 1, $R_1$ and $R_2$ are independently an alkyl group having 1 to 6 carbon atoms or an aryl group having 6 to 12 carbon atoms.

11. The compound of claim 1, wherein $R_3$ is a substituted or unsubstituted alkyl group having 1 to 12 carbon atoms or a substituted or unsubstituted aryl group having 6 to 12 carbon atoms.

12. The compound of claim 1, wherein $R_4$ and $R_5$ are independently a halogen atom, an alkyl group, an alkoxy group, a dialkylamino group or a diarylamino group and each of p and q is an integer of 1 to 3.

13. The compound of claim 12, wherein $R_4$ and $R_5$ are independently an alkyl group or a dialkylamino group and each of p and a is an integer of 1 to 3.

14. The compound of claim 1, wherein $Ar_1$ and $R_1$, or $Ar_2$ and $R_2$ are taken together either directly or indirectly to form a 5- to 7-membered ring.

15. The compound of claim 1, wherein the positions of $Ar_1(R_1)C=CH-(CH=CH)_m-$ and $Ar_2(R_2)C=CH-(CH=CH)_n-$ on the respective benzene rings are the 2-position and the 8-position, respectively.

16. The compound of claim 1, wherein m and n each represent 0 or 1.

17. The compound of claim 1, wherein p and q each represent 0 or 1.

18. The compound of claim 16, wherein m and n each represent 0.

19. The compound of claim 17, wherein p and q each represent 0.

20. A compound represented by formula (IA):

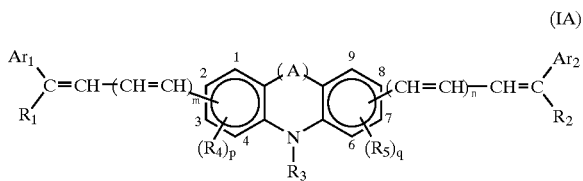

(IA)

wherein (A) represents an ethylene group, a vinylene group or an o-arylene group; $Ar_1$ and $Ar_2$ are each selected from the group consisting of substituted or unsubstituted phenyl, substituted or unsubstituted naphthyl, substituted or unsubstituted phenanthrenyl and substituted or unsubstituted pyrenyl groups; $R_1$ and $R_2$ each represent an alkyl group or an aryl group; $R_3$ represents an alkyl group or an aryl group; $R_4$ and $R_5$ each represent a halogen atom, an alkyl group, an aryl group, an alkoxy group, an aryloxy group, a dialkylamino group, an N-alkyl-N-arylamino group or a diarylamino group; or $Ar_1$ and $R_1$, or $Ar_2$ and $R_2$ are taken together either directly or indirectly to form a ring; $Ar_1(R_1)C=CH-(CH=CH)_m-$ and $Ar_2(R_2)C=CH-(CH=CH)_n-$ are on the 2- or 3-position and the 7- or 8-position of the respective benzene rings; m and n each represent an integer of from 0 to 2; and p and q each represent an integer of from 0 to 3.

21. A compound represented by formula (IA):

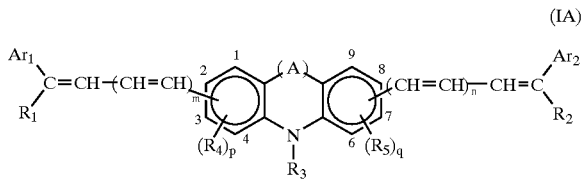

(IA)

in which (A) represents an ethylene group, a vinylene group or an o-arylene group; $Ar_1$ and $Ar_2$ each represent an aryl group; $R_1$ and $R_2$ are independently a straight-chain or branched alkyl group having 1 to 20 carbon atoms or an aryl group having 6 to 36 carbon atoms; $R_3$ represents an alkyl group or an aryl group; $R_4$ and $R_5$ each represent a halogen atom, an alkyl group, an aryl group, an alkoxy group, an aryloxy group, a dialkylamino group, an N-alkyl-N-arylamino group or a diarylamino group; or $Ar_1$ and $R_1$, or $Ar_2$ and $R_2$ are taken together either directly or indirectly to form a ring; $Ar_1(R_1)C=CH-(CH=CH)_m-$ and $Ar_2(R_2)C=CH-(CH=CH)_n-$ are on the 2- or 3-position and the 7- or 8-position of the respective benzene rings; m and n each represent an integer of from 0 to 2; and p and q each represent an integer of from 0 to 3.

22. A compound represented by formula (IA):

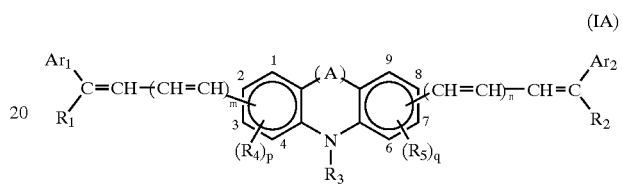

(IA)

wherein (A) represents an ethylene group, a vinylene group or an o-arylene group; $Ar_1$ and $Ar_2$ each represent an aryl group; $R_1$ and $R_2$ each represent an alkyl group or an aryl group; $R_3$ represents an alkyl group or an aryl group; $R_4$ and $R_5$ are independently a halogen atom, an alkyl group, an alkoxy group, a dialkylamino group or a diarylamino group; or $Ar_1$ and $R_1$, or $Ar_2$ and $R_2$ are taken together either directly or indirectly to form a ring; $Ar_1(R_1)C=CH-(CH=CH)_m-$ and $Ar_2(R_2)C=CH-(CH=CH)_n-$ are on the 2- or 3-position and the 7- or 8-position of the respective benzene rings; m and n each represent an integer of from 0 to 2; and p and q each represent an integer of from 1 to 3.

* * * * *